United States Patent
Dehottay et al.

(10) Patent No.: US 9,701,936 B2
(45) Date of Patent: Jul. 11, 2017

(54) FERMENTATION OF FASTIDIOUS BACTERIAL STRAIN IN PERFUSION SUSPENSION CULTURE

(71) Applicant: GlaxoSmithKline Biologicals S.A., Rixensart (BE)

(72) Inventors: Philippe Marc Helene Dehottay, Rixensart (BE); Michael Lanero Fidalgo, Rixensart (BE); Dominique Janssens, Rixensart (BE); Marc Roger Fernand Orval, Rixensart (BE)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

(21) Appl. No.: 14/408,415

(22) PCT Filed: Jun. 24, 2013

(86) PCT No.: PCT/EP2013/063148
§ 371 (c)(1),
(2) Date: Dec. 16, 2014

(87) PCT Pub. No.: WO2014/001261
PCT Pub. Date: Jan. 3, 2014

(65) Prior Publication Data
US 2015/0166948 A1 Jun. 18, 2015

Related U.S. Application Data

(60) Provisional application No. 61/663,697, filed on Jun. 25, 2012.

(30) Foreign Application Priority Data

Jun. 25, 2012 (GB) .................................. 1211256.1

(51) Int. Cl.
| | | |
|---|---|---|
| C12N 1/20 | (2006.01) | |
| C12M 1/00 | (2006.01) | |
| C12M 1/12 | (2006.01) | |
| C12M 1/26 | (2006.01) | |
| C12P 21/00 | (2006.01) | |
| C12P 1/04 | (2006.01) | |
| A61K 39/09 | (2006.01) | |
| A61K 39/095 | (2006.01) | |
| C07K 1/14 | (2006.01) | |
| C12P 19/00 | (2006.01) | |

(52) U.S. Cl.
CPC .............. *C12N 1/20* (2013.01); *A61K 39/092* (2013.01); *A61K 39/095* (2013.01); *C07K 1/145* (2013.01); *C12M 21/14* (2013.01); *C12M 25/02* (2013.01); *C12M 29/10* (2013.01); *C12M 29/12* (2013.01); *C12M 33/14* (2013.01); *C12M 47/04* (2013.01); *C12P 1/04* (2013.01); *C12P 19/00* (2013.01); *C12P 21/00* (2013.01); *C12N 2521/00* (2013.01)

(58) Field of Classification Search
CPC ............ C12N 1/20; C12P 1/04; A61K 39/095
See application file for complete search history.

(56) References Cited

U.S. PATENT DOCUMENTS

| 5,342,781 A | 8/1994 | Su Wie et al. |
| 6,544,424 B1 | 4/2003 | Shevitz et al. |
| 2012/0135470 A1 | 5/2012 | De Rosa et al. |

FOREIGN PATENT DOCUMENTS

| EP | 2 020 433 A2 | 2/2009 |
| EP | 2 308 958 A2 | 4/2011 |
| WO | 2007/071072 A1 | 6/2007 |

OTHER PUBLICATIONS

Baart et al. "Scale-up for bulk production of vaccine against meningococcal disease" (2007) Vaccine, vol. 25: 6399-6408.*

* cited by examiner

*Primary Examiner* — Teresa E Knight
(74) *Attorney, Agent, or Firm* — Virginia G. Campen

(57) ABSTRACT

The present invention relates to improved processes for culturing bacteria, in particular to processes for perfusion suspension culturing of bacteria in a fermenter, wherein the culture medium including the bacteria is circulated over a separation system in alternating tangential flow, wherein the separation system removes a filtrate containing inhibitory metabolites from the culture medium.

17 Claims, 15 Drawing Sheets

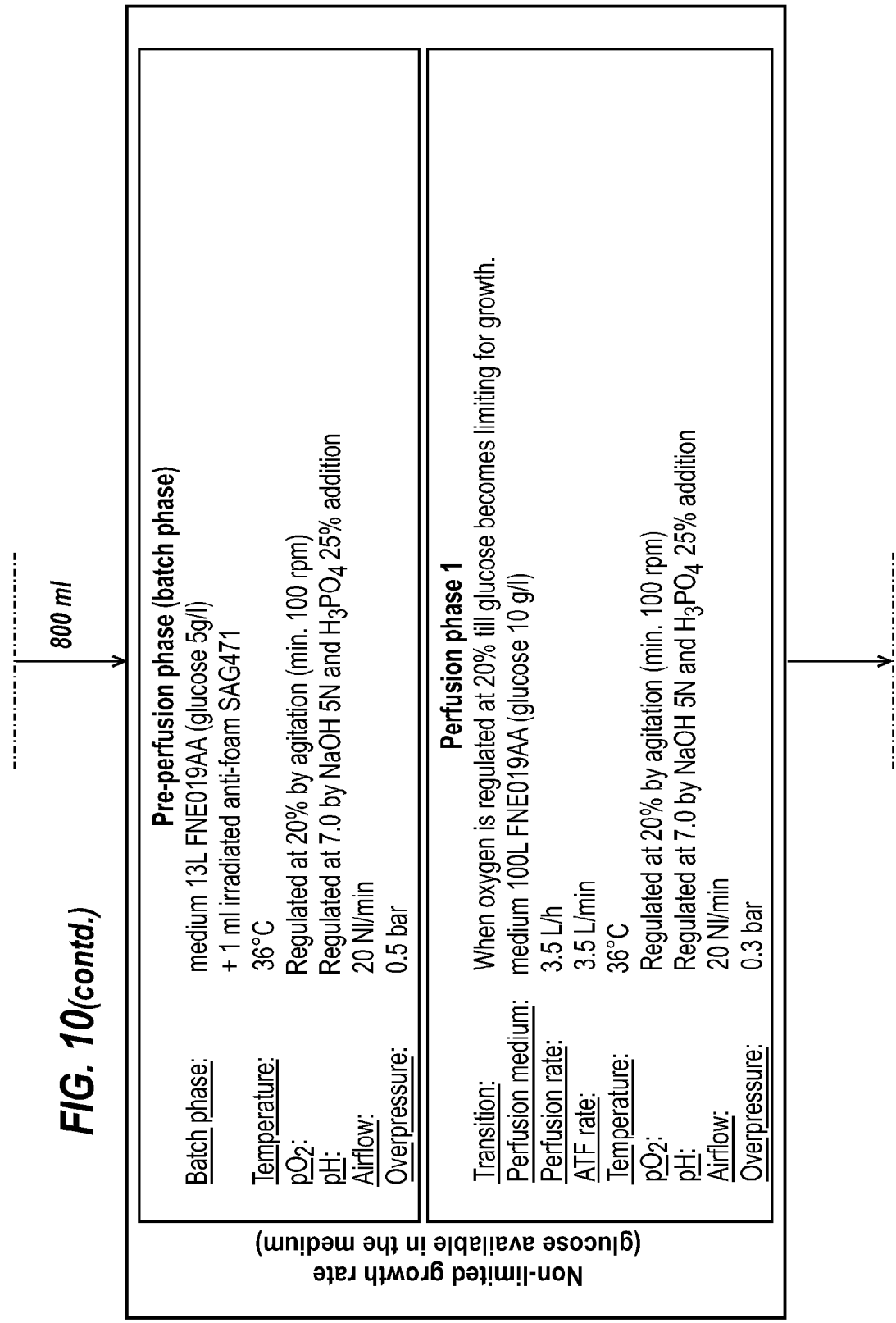
FIG. 10 (contd.)

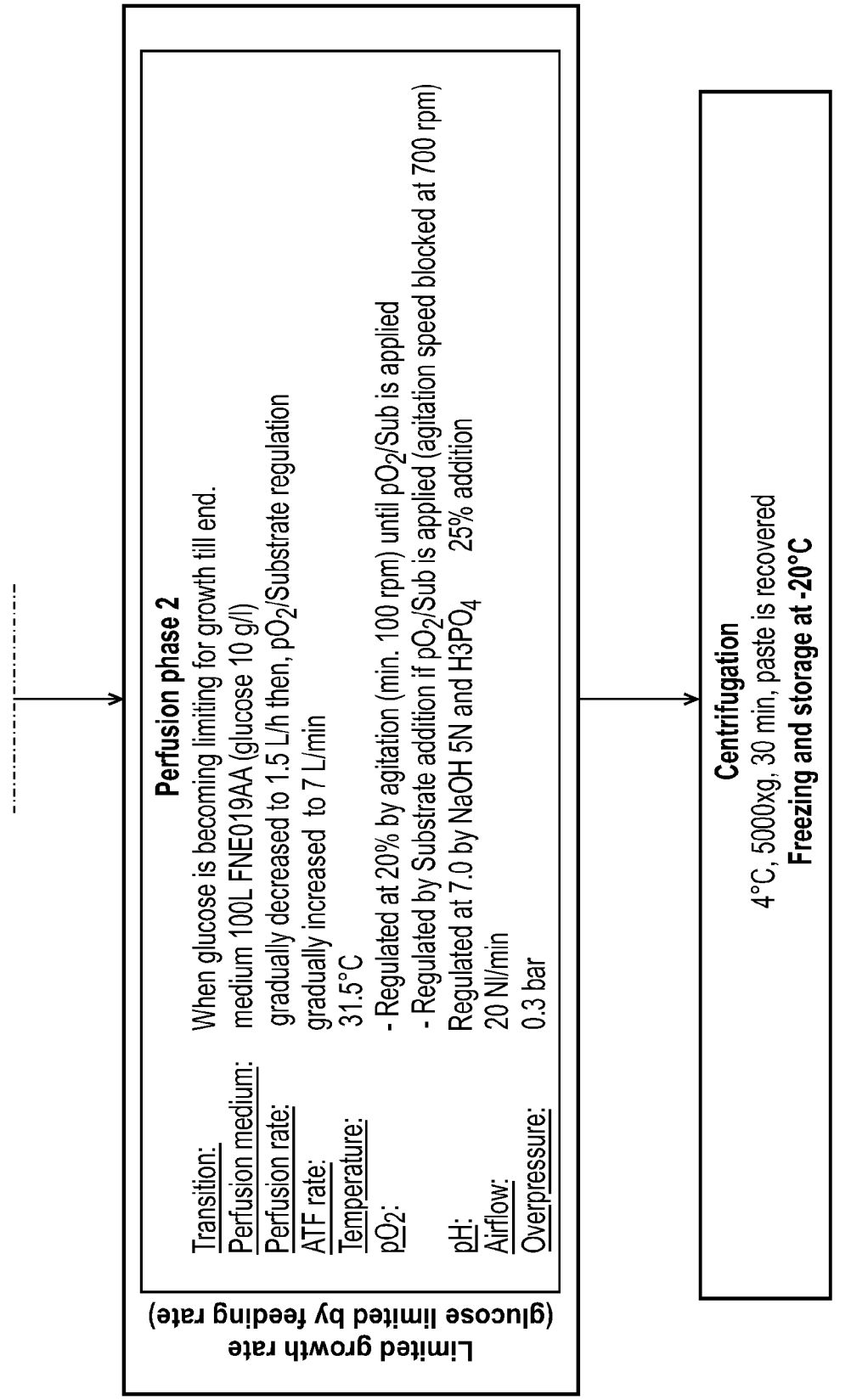
FIG. 10(contd.)

FERMENTATION OF FASTIDIOUS BACTERIAL STRAIN IN PERFUSION SUSPENSION CULTURE

This application is filed pursuant to 35 U.S.C. §371 as a United States National Phase Application of International Patent Application Serial No. PCT/EP2013/063148 filed Jun. 24, 2013, which claims priority to U.S. Patent Application No. 61/663,697 filed Jun. 25, 2012 and Great Britain Patent Application No. 1211256.1 filed Jun. 25, 2012 the contents of each of the foregoing applications are hereby incorporated by reference.

All references or patent applications cited within this patent specification are incorporated by reference herein.

TECHNICAL FIELD

The present invention relates to the field of fermentation, in particular to improved processes for culturing bacteria.

BACKGROUND

Bacteria are widely used in life science, as source for food products, for vaccine components and for biotechnological production of recombinant proteins. For production-scale microbial fermentations, high cell densities are often desired and thus much research and effort has been put into optimization of culture conditions.

Generally, cell culture and microbial fermentation can be performed in batch, fed-batch, continuous or perfusion mode, or in combinations thereof.

Animal cells generally grow slowly, are fragile and necessitate gentle culture conditions. For animal cells, perfusion culture is the preferred mode. In perfusion mode, feed solutions are fed to a bioreactor continuously and spent medium is constantly removed. The advantage of perfusion culture over fed-batch culture is that if any inhibitory metabolites are generated during growth, these metabolites will continuously be removed and thus their growth inhibitory effect will be minimized. During perfusion culture, the majority of the animal cells is retained in the bioreactor. This is often achieved by filtration. In such set-ups, high tangential velocity generated by crossflow or spinning filters may be used to keep the filter surfaces clean. Also, methods based on alternating tangential flow (ATF) have been developed which cause animal cell aggregates to wash back into the vessel removing a potential blockage (see e.g. U.S. Pat. No. 6,544,424, Furey J (2002) Genetic Engineering News 22: 62-63 and WO2005095578).

Compared with animal cells, bacterial growth rates are generally much faster and necessitate higher feeding rate, and lead to faster accumulations of inhibitory products. Consequently, industrial scale fermentation of bacteria is mostly done in batch or fed-batch mode. Efforts to obtain higher yields have mainly focussed on the improvement of culture media including increased agitation rates and vigorous delivery of gases into the culture and controlled feeding strategies which are not applicable to animal cell culture, which requires more gentle conditions. Perfusion-like forms of culturing bacteria, such as dialysis culture, have been successful with a number of bacteria (Schultz and Gerhardt (1969) Microbiol. Mol. Biol. Rev 33:1), including *Neisseria gonorrhoeae* (Gerhardt and Heden (1960) Proc. Soc. Exp. Biol. Med. 105:49) but are generally difficult to scale-up. Jung and Lowitt ((2010), J Chem Technol Biotechnol, 85: 1250-1259) describe perfusion culture of lactic acid bacteria in a pilot scale membrane bioreactor. The growth of bacteria were restricted due to serious membrane fouling on the product membrane by extracellular lipopolysaccharides and glycoproteins.

Fuchs et al. (2002) J. Biotechnol. 93:243 describe a scaled-up dialysis fermentation method for *Escherichia coli* which results in increased cell densities and protein production. There remains a need for easy, robust, and upscalable methods for the fermentation of bacteria, in particular fastidious bacteria, which result in high cell densities and/or high production of biopolymers.

SUMMARY OF THE INVENTION

It has now surprisingly been found that large-scale perfusion culture of bacteria making use of alternating tangential flow (ATF) over a filter results in a high yield of cellular biomass and/or biopolymers, even for a strain of a fastidious bacterium, such as *Neisseria meningitidis*, and *Streptococcus pneumoniae* as exemplified herein. Thus, even large-scale culture of fast-growing organisms, such as bacteria, under known media and growth conditions can be improved by a switch to perfusion mode making use of tangential flow or ATF. It is hypothesized that this is due to efficient removal of growth inhibitory metabolites by using this perfusion mode. Some bacteria such as *Neisseria meningitidis*, and *Streptococcus pneumoniae* may produce significant amounts of high molecular weight molecules, such as capsular polysaccharides, lipopolysaccharides, or glycoproteins with high yield, resulting in a viscous fermentation broth which may lead to membrane fouling in conventional systems. Membrane fouling increases the risk of cell lysis, foaming, increased pressure and increased volume in the fermenter. Use of alternating tangential flow is beneficial in that it delays or reduces membrane fouling.

Accordingly, in a first aspect, there is provided a process for culturing a bacterial strain in a fermenter comprising the steps of: a) adding a liquid growth medium to a fermenter; b) seeding the growth medium with the bacteria to form a culture medium; c) growing the bacteria in perfusion suspension culture, wherein the culture medium including the bacteria is circulated over a separation system in alternating tangential flow, and the separation system removes a filtrate containing spent medium from the culture medium and retains the bacteria in the culture medium.

When used herein, the phrase "retains the bacteria in the culture medium" or similar phrases mean that the large majority of the bacteria, such as more than 95%, more than 99% or more than 99.9% of the bacteria are retained in the culture medium. The spent medium may contain some of the bacteria.

In one embodiment, the spent medium contains inhibitory metabolites.

In one embodiment, the bacterial strain is a fastidious bacterial strain.

In a further embodiment, the bacterial strain is selected from the group consisting of *Bordetella pertussis*, *Neisseria meningitidis*, *Cornyebacterium diphtheriae*, *Clostridium tetani*, *Clostridium difficile*, *Helicobacter pylori*, *Haemophilus influenzae*, *Staphylococcus aureus*, *Streptococcus pneumoniae*, *Salmonella*, *Spirochetes*, *Legionella* species and *Mycobacterium tuberculosis*.

In a further embodiment, the bacterial strain is a strain of *Neisseria meningitidis*, in particular a strain selected from the group consisting of *Neisseria meningitidis*, *Neisseria meningitidis* serogroup A, *Neisseria meningitidis* serogroup B, *Neisseria meningitidis* serogroup C, *Neisseria meningiti-*

*dis* serogroup W135 and *Neisseria meningitidis* serogroup Y. In a particular embodiment the bacterial strain is *Neisseria meningitidis* serogroup B.

In a further embodiment, the bacterial strain is a strain of *Streptococcus pneumoniae*, such as *Streptococcus pneumoniae* serotype 1, 4, 5, 6A, 6B, 7F, 9V, 12F, 14, 15C, 33F, 18C, 19A, 19F, 22F or 23, in particular *Streptococcus pneumoniae* serotype 22F.

In one embodiment, the bacterial strain is not a strain of *Escherichia coli*.

The fermenter used in the process of the invention may be any apparatus suitable for the industrial production of bacterial perfusion cultures, such as a fermenter suitable for culturing a suspension having a volume of at least 10 liters, such as at least 20 liters, e.g. at least 50 liters, such as at least 100 liters, e.g. at least 250 liters.

If hollow fiber membranes are used in the separation system, the alternating tangential flow (ATF) may comprise a first flow in the same direction as the membrane surfaces of the hollow fibers, which flow reverses direction intermittently, and a second flow in a direction substantially perpendicular to said membrane surface. Tangential flow may be achieved according to methods known to the person skilled in the art. For example, in U.S. Pat. No. 6,544,424 it is described that alternating tangential flow may be achieved using one pump to circulate the cell culture over a filter module comprising hollow fibers and another pump to remove liquid having a lower cell density than prior to the filter separation.

Suitable ATF systems for use in the process of the present invention include the ATF systems developed by Refine Technology, for example ATF2 (<10 L of culture), ATF4 (10-50 L), ATF6 (50-250 L) ATF8 (250-1000 L) or ATF10 (>1000 L).

Alternative suitable systems include vibrating membrane filtration technology systems, optionally with a recirculation flow or tangential flow filtration system, for example having hollow fiber membranes, with a recirculating flow.

In one embodiment, the separation system comprises a filter module comprising hollow fibre membranes suitable for the removal of inhibitory metabolites from the culture medium. In a further embodiment, the separation system comprises a filter module comprising hollow fibres, e.g. hollow fibres made of polysulphone, having a porosity of between 0.4 μm and 0.1 μm, e.g. a porosity of 0.2 μm. In another embodiment, the separation system comprises a filter module comprising membranes wherein the membranes have a molecular weight cut-off pore size of between 500,000 and 5,000 Da, between 20,000 and 1,000 Da or below 5,000 Da.

In one embodiment, the fermentation is carried out under current Good Manufacturing Practices.

Liquid media for the growth of bacteria are well-known in the art. Liquid media for the growth of fastidious bacteria, which have more complex requirements, have also been described. In one embodiment of the process of the invention, the liquid medium comprises, or consists of, amino acids, a carbon source (such as glucose), and inorganic salts in a buffered aqueous solution. One of the constituents of the medium may function as buffer or a buffer component may be added.

In a further embodiment, the liquid medium used in the process, in particular useful for growing *N. meningitidis*, comprises or consists of glutamic acid, glucose and inorganic salts, optionally supplemented with soy peptone and/ or cysteine. In an even further embodiment of the process, the bacterial strain is a strain of *N. meningitidis* and the medium is, or is essentially, the "final" medium described in Frantz (J. Bact. 43(6): 757-761 (1942)), optionally further supplemented with soy peptone.

In other embodiments, the culture medium used for growing *S. pneumoniae* is substantially the medium described in Hoeprich (J. Bact. 69(6): 682-688 (1955)) in which the component concentrations were adapted in order to optimize the biomass and yield of capsular polysachharide.

The fermentation step may produce a large amount of foam. In order to control foam formation an anti-foam agent is optionally added to the fermenter. Optionally a foam probe or mechanical foam breaker is used in the fermenter, for example in addition to the anti-foam agent. One step of the process of the invention (perfusion suspension culture phase) comprises growing bacteria in perfusion suspension culture, wherein the culture medium including the bacteria is circulated over a separation system in tangential flow, wherein the separation system removes a filtrate containing inhibitory metabolites from the culture medium and retains the bacteria in the culture medium.

In some embodiments, feed and perfusion rates may be coupled and controlled by the same pump. Feed and perfusion rates may be altered simultaneously or separately. Where a measurement or alteration of perfusion rate is referred to below, this may either refer to perfusion rate alone or in combination with the feed rate. In order to facilitate optimisation of feed or perfusion rate they may be automated or controlled manually. In some embodiments, the medium feeding rate or the spent medium withdrawal rate, or both, may be adjusted to limit the accumulation of inhibitory metabolites in order to reduce or avoid inhibitory effect on the culture.

In some embodiments this may be done using dissolved oxygen measurement in the fermenter. In other embodiments, the feed and perfusion rates may be controlled to maintain lactic acid at a controlled level. This may be done with the use of a conductivity sensor in the fermenter.

Some embodiments include a pre-perfusion culture phase which has a perfusion rate of zero. For example, the level of nutrients will often initially be high enough for the culture to be able to grow without addition of fresh medium and the level of inhibitory metabolites in the culture medium will often initially be low enough to allow growth of the culture without removal of the filtrate. Thus, in such a situation perfusion may not need to be initiated at the start of fermentation, as this may not provide any growth benefit. The time point at which perfusion needs to be initiated to maintain acceptable growth will vary, depending, inter alia, on the bacterial strain, the composition of the media, and culture conditions.

In one embodiment, the pre-perfusion culture phase wherein the perfusion rate is zero is maintained until the dissolved oxygen has reached a certain level or set point, for example a level of about 20% of the initial level, such as a level of 20% of the initial level of dissolved oxygen reached using an aeration rate of 20 Nl/min (or equivalent level of dissolved oxygen using a different aeration rate). "Initial level" in this context means the level of dissolved oxygen at the start of the fermentation.

In another embodiment, the pre-perfusion culture phase which has a perfusion rate of zero has a duration of 1 to 10 hours, such as 1 to 5 hours, e.g. 2 hours.

The perfusion suspension culture phase is typically initiated when the level of nutrients in the culture and/or the level of inhibitory metabolites in the culture becomes limiting for growth. Initiating perfusion typically becomes beneficial as soon as one of these two factors becomes limiting. For example, in one embodiment, perfusion is initiated to remove inhibitory metabolites, even though the level of nutrients, e.g. the carbon source, such as glucose, glycerol or glutamate, is not yet exhausted.

The rate of the perfusion (i.e. the volume of medium passing through the system per time unit) may vary depending on the circumstances, including the type of bacteria and growth rate. In some embodiments, the perfusion rate is kept constant during the perfusion suspension culture phase. In other embodiments, the rate of perfusion is increased or decreased depending upon the degree or rate of growth of bacteria in perfusion suspension culture. This may be stepwise or gradually.

In one embodiment, the perfusion suspension culture phase has an average perfusion rate of above 5% of the culture volume per hour, i.e. for example in a 20-liter culture, more than 1 liter of culture is added and removed per hour. In other embodiments, the average perfusion rate is above 10% of the culture volume per hour, such as above 15%, e.g. above 20%, such as above 30%, e.g. above 50%, such as above 75% of the culture volume per hour. In further embodiments, the average perfusion rate is between 5% and 100%, such as between 5% and 50%, e.g. between 5% and 20%, such as between 10% and 20% of the culture volume per hour.

In some embodiments, the perfusion rate is changed during the fermentation, according to the composition of the culture. For example, after some time of perfusion, the nutrient composition in the culture may become stable because nutrients in the initial batch of media have become exhausted. At this point, the perfusion rate may be increased or decreased. For example, in one embodiment, the perfusion rate is reduced when the carbon source in the medium is exhausted. The carbon source may be for example glucose, glycerol or glutamate. The perfusion rate may be reduced 1.5 or 2 fold during the perfusion suspension culture phase when the carbon source in the medium is exhausted, and optionally kept a constant rate until the end of the fermentation. An advantage of reducing the perfusion rate may be that it limits the growth rate due to limiting the flow of new nutrients. The control of the growth rate may help to avoid any limitation of oxygen transfer rate that could lead to cell lysis and subsequent ATF membrane fouling.

In other embodiments, the perfusion rate is increased during the perfusion suspension culture phase, such as increased by at least 1.5, at least 2, at least 3, at least 4 or at least 5 fold during the perfusion suspension culture phase.

In even further embodiments, after exhaustion of the carbon source, the perfusion rate is automatically controlled by the oxygen demand. Thus, after the point in time when the carbon source, such as glucose, glycerol or glutamate, becomes limiting for growth, the perfusion rate is automatically controlled by oxygen demand (pO2/substrate regulation), by decreasing perfusion rate when dissolved oxygen drops below a certain predefined level and increasing the rate when dissolved oxygen exceeds a certain predefined level. To ensure a constant and non-limiting oxygen supply the agitation speed may be kept constant. In one embodiment, the level of dissolved oxygen is kept between 10% and 30%, such between 15% and 25%, e.g. at 20% of the initial level, such as a level of between 10% and 30%, such as between 15% and 25%, e.g. at 20% of the initial level of dissolved oxygen reached using an aeration rate of 20 Nl/min or equivalent level of dissolved oxygen using a different aeration rate.

In some embodiments, the medium feeding rate and the spent medium withdrawal rates may be adjusted to limit the accumulation of lactic acid to a value which has low or no inhibitory effect on the culture. Biomass, lactic acid concentration, instantaneous rate of base addition or conductivity are each measurements that may be used to control the perfusion rate either manually or automatically.

The duration of the perfusion suspension culture phase of the process of the invention) may vary. Typically the culture is continued until the cell density no longer increases, until cell lysis is observed or until sufficient yield has been obtained. In embodiments wherein a biopolymer is produced, the perfusion suspension culture phase may continue until no significant further amounts of the biopolymer are obtained, for example in the filtrate. In one embodiment, the perfusion suspension culture phase has a duration of at least 6, at least 8, at least 12, at least 16, at least 20, at least 24, at least 28, at least 36, or at least 48 hours. In another embodiment, the duration of the perfusion suspension culture phase is between 6 and 48 hours, such as between 16 and 48 hours.

The volume of the suspension culture in the process of the invention may vary according to the particular circumstances. The process of the invention has the advantage that it is relatively easy to scale up compared to other perfusion-type process.

In one embodiment, the suspension culture has a volume of at least 10 liters, such as at least 20 liters, at least 50 liters, at least 100 liters, at least 200, or at least 250 liters, or at least 500 liters, or between 500 and 1000 liters, such as 700 liters.

In one embodiment, the initial liquid growth medium contains less than 50, less than 30, less than 20, less than 15, less than 10 or less than 5 g/L of glucose. In a further embodiment of the process, glucose levels in the culture medium are below 40, below 30, below 20, below 10, below 5, below 4, below 3, below 2, below 1 or below 0.5 g/L after at least 1, at least 2, at least 3, at least 4, at least 5, at least 7, at least 10, at least 12 or at least 15 hours of the perfusion suspension culture phase.

The temperature of the suspension culture will usually depend on the bacterial strain that is being propagated. The temperature may be kept constant throughout the process, or it may be changed. In some embodiments, after the point in time when the carbon source becomes limiting for growth, the temperature may be reduced for the remaining period of the fermentation. In one embodiment, the temperature may be kept constant at about 36° C. until the glucose in the media is exhausted and then reduced to a temperature below 36° C., such as below 35° C., e.g. between 30° C. and 34° C., such as 31.5° C., e.g. for the remaining period of the fermentation. This temperature profile may be used where the bacterial strain that is grown is a strain of *N. meningitides* or *Streptococcus pneumoniae*.

The pH of the culture may be controlled during the perfusion suspension culture phase of the process and e.g. be kept at 7.0 to 7.5.

The agitation speed may be kept constant or may vary, the speed may e.g. be between 100 rpm and 1000 rpm.

In one embodiment, the pressure in the vessel is at most 0.7 bar, at most 0.5 bar, at most 0.3 bar, at most 0.2 bar, or between 0.02 and 0.2 bar, e.g. 0.1 bar, during the perfusion suspension culture phase. In another embodiment, the pressure is reduced when the dissolved oxygen reaches its regulation setpoint or at a point in time thereafter, e.g. the pressure may be reduced 1.5 to 2 fold when the dissolved oxygen reaches its regulation setpoint, for example reduced from 0.5 to 0.3 bar.

The process of the invention results in cell densities that may be quantified by determining the optical density (OD)

at 650 nm. In one embodiment, the density of the bacteria reaches at least 10, at least 15, at least 20, at least 30, at least 40, at least 50, at least 60, or at least 70 OD units measured at 650 nm at the end of fermentation.

As explained above, during the perfusion suspension culture phase of the process of the invention, the separation system removes a filtrate containing spent medium which may contain inhibitory metabolites from the culture medium.

In some embodiments medium may be fed to the fermentation system simultaneously to extraction of spent medium.

In some embodiments, acetate is the, or one of the, inhibitory metabolites. Thus, in one embodiment of the process, acetate levels in the culture medium remain below 4, below 3, below 2, below 1 or below 0.5 g/L throughout the perfusion suspension culture phase. In other embodiments, acetate levels are higher in an early phase of the fermentation, but are below 4, below 3, below 2, below 1 or below 0.5 g/L after at least 5, at least 7, at least 10, at least 12 or at least 15 hours of the perfusion suspension culture phase. Acetate levels can, for example, be measured using gas chromatography.

In other embodiments, ethanol is the, or one of the, inhibitory metabolites. Thus, in one embodiment of the process, ethanol levels in the culture medium remain below 0.6, below 0.5, below 0.4, below 0.2 or below 0.1 g/L throughout the perfusion suspension culture phase. In other embodiments, ethanol levels are higher in an early phase of the fermentation, but are below 0.6, below 0.5, below 0.4, below 0.2 or below 0.1 g/L after at least 5, at least 7, at least 10, at least 12 or at least 15 hours of the perfusion suspension culture phase.

Ethanol levels can be measured using gas chromatography, for example.

In a further embodiment, acetate levels in the culture medium remain below 4, below 3, below 2, below 1 or below 0.5 g/L throughout step c) and ethanol levels in the culture medium remain below 0.6, below 0.5, below 0.4, below 0.2 or below 0.1 g/L throughout the perfusion suspension culture phase.

In other embodiments, lactate is the, or one of the, inhibitory metabolites. Thus, in one embodiment of the process, lactate levels in the culture medium remain below 30, below 25, below 20, below 15 or below 10 g/L throughout the perfusion suspension culture phase. Lactate level can, for example, be measured by enzymatic assay using YSI lactate analyser.

In a further aspect, there is provided a culture of bacteria in a fermenter having an optical density (OD) of at least 10, at least 15, at least 20, at least 30, at least 40, at least 50, at least 60, or at least 70 OD units measured at 650 nm.

In one embodiment, the culture of bacteria is a culture of a fastidious bacterial strain.

In one embodiment, the culture of bacteria is a culture of a bacterial strain selected from the group consisting of *Bordetella pertussis, Neisseria meningitidis, Cornyebacterium diphtheriae, Clostridium tetani, Clostridium difficile, Helicobacter* pylori; *Haemophilus influenzae, Streptococcus pneumoniae, Spirochetes* species, *Legionella* species, and *Mycobacterium tuberculosis*.

In a further embodiment, the culture of bacteria is a culture of *Neisseria meningitidis*, selected from the group consisting of *Neisseria meningitidis* serogroup A, *Neisseria meningitidis* serogroup B, *Neisseria meningitidis* serogroup C, *Neisseria meningitidis* serogroup W135 and *Neisseria meningitidis* serogroup Y. In a particular embodiment the culture of bacteria is a culture of *Neisseria meningitidis* serogroup B.

In a further embodiment, the culture of bacteria is a culture of *Streptococcus pneumoniae*, such as *Streptococcus pneumoniae* serotype 1, 4, 5, 6A, 6B, 7F, 9V, 12F, 14, 15C, 33F, 18C, 19A, 19F, 22F or 23, in particular *Streptococcus pneumoniae* serotype 22F.

In another aspect, there is provided a process for producing a biopolymer or an aggregate of biopolymers including the steps of i) culturing a bacterial strain according to the process of the invention and ii) harvesting the biopolymer or aggregate thereof from the culture medium or filtrate.

In a further aspect, there is provided a biopolymer or aggregate of biopolymers obtained or obtainable by the process of the invention.

The biopolymers or aggregates of biopolymers may be naturally produced by the bacteria and, for example, may be useful as antigens for the production of an immunogenic composition to be used as a vaccine. Alternatively, genetically modified bacteria may be used to produce biopolymers or aggregates of biopolymers that are not naturally produced by the bacterial strain.

In one embodiment, the biopolymer or aggregate thereof is a polysaccharide, such as a polysaccharide which is naturally produced by the strain that is cultured. In another embodiment, the biopolymer or aggregate thereof is a protein, such as a protein which is naturally produced by the strain that is cultured. In a further embodiment, the biopolymer is a bacterial toxin or toxoid. In another embodiment, the biopolymer or aggregate thereof is a recombinant protein, which is produced from a heterologous gene which has been introduced into the bacterial strain. Methods for genetic engineering of bacteria are well-known in the art.

Recombinant proteins may be expressed from a plasmid. The promoter used may be the promoter that is naturally associated with said gene, or a promoter of a different origin.

If the promoter used for the production of the recombinant protein is an inducible promoter, for example an IPTG-inducible promoter, the induction is typically performed when a suitable cell density has been obtained in the fermenter. For example, expression of the heterologous gene may be induced at the time of inoculation, or during fermentation, for example at a time when the cell density has reached at least 25%, at least 50%, at least 75% or at least 100% of the expected final cell density.

In a further embodiment, the aggregate of biopolymers is an outer membrane vesicle or bleb.

In one embodiment of the process for producing a biopolymer or aggregate thereof the bacterial strain is an outer membrane vesicle producing strain of Gram negative bacteria. The biopolymer or aggregate thereof produced may be a protein or an outer membrane vesicle.

In another embodiment, the bacterial strain is from *Neisseria meningitidis*, optionally from serogroup B. The biopolymer produced may be a polysaccharide, such as a capsular polysaccharide.

In a further embodiment, the bacterial strain is from *Neisseria meningitidis* serogroup A, C, W135 or Y. The biopolymer produced may be a polysaccharide, such as a capsular polysaccharide.

In a further embodiment of the process for producing a biopolymer or aggregate thereof, the bacterial strain is from *Bordetella pertussis*. The biopolymer produced may e.g. be pertussis toxin, 69 kDa pertactin or filamentous hemagglutinin.

In a further embodiment, the bacterial strain is *Streptococcus pneumoniae*, such as *Streptococcus pneumoniae* serotype 1, 4, 5, 6A, 6B, 7F, 9V, 12F, 14, 15C, 33F, 18C, 19A, 19F, 22F or 23, in particular *Streptococcus pneumoniae* serotype 22F. The biopolymer produced may be a polysaccharide or a protein. In one embodiment, the biopolymer produced is the 22F capsular polysacharride.

In an even further embodiment, the process for producing a biopolymer or aggregate thereof comprises a further step of conjugating the biopolymer or aggregate thereof to a saccharide. The term "saccharide" throughout this specification may indicate polysaccharide, oligosaccharide or teichoic acid and includes all three. It may indicate lipopolysaccharide (LPS) or lipooliogosaccharide (LOS). Before use Polysaccharides may be isolated from a source strain and sized to some degree by known methods (see for example EP497524 and EP497525; Shousun Chen Szu et al. —Carbohydrate Research Vol 152p 7-20 (1986)) for instance by microfluidisation. Oligosaccharides have a low number of repeat units (typically 5-30 repeat units). In another embodiment, the process for producing a biopolymer or aggregate thereof comprises a further step of conjugating the biopolymer or aggregate thereof to a carrier protein.

The term "carrier protein" is intended to cover both small peptides and large polypeptides (>10 kDa). The carrier protein may be any peptide or protein. It may comprise one or more T-helper epitopes. The carrier protein may be tetanus toxoid (TT), tetanus toxoid fragment C, non-toxic mutants of tetanus toxin [note all such variants of TT are considered to be the same type of carrier protein for the purposes of this invention], diphtheria toxoid (DT), CRM197, other non-toxic mutants of diphtheria toxin [such as CRM176, CRM 197, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709, 017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843,711] (note all such variants of DT are considered to be the same type of carrier protein for the purposes of this invention), pneumococcal pneumolysin (Kuo et al (1995) Infect Immun 63; 2706-13), OMPC (meningococcal outer membrane protein—usually extracted from *N. meningitidis* serogroup B-EP0372501), synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of *C. difficile* (WO 00/61761), *H. influenzae* Protein D (EP594610 and WO 00/56360), pneumococcal PhtA (WO 98/18930, also referred to Sp36), pneumococcal PhtD (disclosed in WO 00/37105, and is also referred to SpO36D), pneumococcal PhtB (disclosed in WO 00/37105, and is also referred to SpO36B), or PhtE (disclosed in WO00/30299 and is referred to as BVH-3).

In one embodiment of the invention the carrier protein is selected from the group consisting of: tetanus toxoid (TT), fragment C of tetanus toxoid, diphtheria toxoid (DT), CRM197, Pneumolysin (Ply), protein D, PhtD, PhtDE and N19. In a further embodiment the carrier protein is CRM197. In a still further embodiment the carrier protein is tetanus toxoid.

Step ii) of the process for producing a biopolymer or aggregate thereof, i.e. harvesting the biopolymer or aggregate thereof from the culture medium or filtrate, may be performed in different ways, depending mainly on the biopolymer or aggregate thereof.

A biopolymer or aggregate thereof that is not withheld by the separation system and thus is present in the filtrate may be harvested from said filtrate and optionally be purified and/or concentrated.

A biopolymer or aggregate thereof that is withheld by the separation system and thus is retained in the culture medium will be harvested from said culture medium. If the biopolymers or aggregate thereof is cell associated, cells may be collected and optionally subjected to further procedures to isolate, purify and/or concentrate the desired biopolymer or aggregates thereof. These procedures may include lysing or otherwise disrupting the cells.

If the biopolymer or aggregate thereof is not cell associated, steps such as centrifugation may be performed to remove the cells and the biopolymer or aggregate thereof may then be obtained from the remaining medium, optionally via purification and/or concentration.

In an even further aspect, there is provided a process for producing a vaccine comprising the steps of 1) producing a biopolymer or aggregate thereof using the process of the invention and 2) formulating said biopolymer or aggregate thereof as a vaccine by adding a pharmaceutically-acceptable excipient and optionally further antigens and/or adjuvants Vaccine preparation is generally described in Vaccine Design ("The subunit and adjuvant approach" (eds Powell M. F. & Newman M. J.) (1995) Plenum Press New York).

The vaccine may optionally comprise one or more adjuvants in an amount sufficient to enhance the immune response to the immunogen. Suitable adjuvants include, but are not limited to, aluminium salts, squalene mixtures, muramyl peptide, saponin derivatives, *mycobacterium* cell wall preparations, monophosphoryl lipid A, mycolic acid derivatives, non-ionic block copolymer surfactants, Quil A, cholera toxin B subunit, polphosphazene and derivatives, and immunostimulating complexes (ISCOMs).

The vaccine preparations that are produced may be used to protect a mammal (for example a human) susceptible to infection by a pathogen, or to treat a mammal (for example a human) having a pathogen infection, by means of administering said vaccine via systemic or mucosal route, where the vaccine is suitable for prevention and/or treatment of the pathogen.

These administrations may include injection via the intramuscular, intraperitoneal, intradermal or subcutaneous routes; or via mucosal administration to the oral/alimentary, respiratory, genitourinary tracts. Although the vaccine of the invention may be administered as a single dose, components thereof may also be co-administered together at the same time or at different times.

Embodiments of the invention are further described in the subsequent numbered paragraphs.

Paragraph 1: A process for culturing a bacterial strain in a fermenter comprising the steps of:
a) adding a liquid growth medium to a fermenter; b) seeding the growth medium with bacteria to form a culture medium; c) growing the bacteria in perfusion suspension culture, wherein the culture medium including the bacteria is circulated over a separation system in alternating tangential flow, and the separation system removes a filtrate containing spent medium from the culture medium and retains the bacteria in the culture medium.

Paragraph 2: The process according to Paragraph 1 wherein the spent medium contains inhibitory metabolites.

Paragraph 3: The process according to Paragraph 1 or Paragraph 2 wherein the bacterial strain is a fastidious bacterial strain.

Paragraph 4: The process according to any one of the preceding Paragraphs wherein the separation system comprises a filter module comprising hollow fibre membranes for the removal of inhibitory metabolites from the culture medium.

Paragraph 5: The process according to any one of the preceding Paragraphs wherein step c) is preceded by a pre-perfusion phase which has a perfusion rate of zero.

Paragraph 6: The process according to Paragraph 5 wherein the pre-perfusion phase has a duration of 1 to 10 hours, such as 1 to 5 hours, for example 2 hours.

Paragraph 7: The process according to Paragraph 5 wherein the pre-perfusion phase has a duration of 5 to 15 hours, such as 8 to 12 hours.

Paragraph 8: The process according to any one of the preceding Paragraphs wherein step c) has an average perfusion rate of between 5 and 100% of the culture volume per hour, such as 10% or above, or 25% or above of the culture volume per hour.

Paragraph 9: The process according to any one of the preceding Paragraphs wherein the perfusion rate in step c) is reduced when the carbon source in the medium is exhausted.

Paragraph 10: The process according to any of the preceding Paragraphs wherein after a point in time when the carbon source becomes limiting for bacterial growth, the perfusion rate is automatically controlled by oxygen demand, for example wherein dissolved oxygen is kept at about 20% of the initial level.

Paragraph 11: The process according to any preceding Paragraph wherein step c) has a duration of at least 6, at least 8, at least 12, at least 16, at least 20, at least 24, or at least 28 hours.

Paragraph 12: The process according to any preceding Paragraph wherein the suspension culture has a volume of at least 10 liters, such as at least 20 liters, at least 50 liters, at least 100 liters, or at least 250 liters.

Paragraph 13: The process according to any preceding Paragraph wherein the liquid medium comprises, or consists of, amino acids, a carbon source, such as glucose, and inorganic salts in a buffered aqueous solution.

Paragraph 14: The process according to any preceding Paragraph wherein the bacteria are grown at a pressure of at most 0.7 bar, at most 0.5 bar, such as at most 0.3 bar, e.g. at most 0.2 bar, such as between 0.02 and 0.2 bar, e.g. 0.1 bar.

Paragraph 15: The process of any preceding Paragraph, wherein after the point in time when the carbon source becomes limiting for growth, the temperature is reduced to below 36° C., such as below 35° C., e.g. between 30° C. and 34° C., such as 31.5° C. for the remaining period of the fermentation.

Paragraph 16: The process according to any of the preceding Paragraphs wherein the pH of the culture is controlled during the perfusion suspension culture phase of the process.

Paragraph 17: The process according to the preceding Paragraph wherein the pH is maintained at or between 7.0 to 7.5.

Paragraph 18: The process according to the preceding Paragraphs wherein the pH is maintained at about 7.0.

Paragraph 19: The process according to any of the preceding Paragraphs wherein the agitation speed may be kept constant or may vary, the speed may e.g. be between 100 rpm and 1000 rpm.

Paragraph 20: The process of any preceding Paragraph wherein the density of the bacteria reaches at least 10, at least 15, at least 20, at least 30, at least 40, at least 50, at least 60, or at least 70 OD units measured at 650 nm.

Paragraph 21: The process according to any preceding Paragraph wherein the initial liquid growth medium contains less than 50, less than 30, less than 20, less than 15, less than 10 or less than 5 g/L of glucose.

Paragraph 22: The process according to any preceding Paragraph wherein glucose levels in the culture medium are below 40, below 30, below 20, below 10, below 5, below 4, below 3, below 2, below 1 or below 0.5 g/L after at least 1, at least 2, at least 3, at least 5, at least 7, at least 10, at least 12 or at least 15 hours of of the perfusion suspension culture phase step c).

Paragraph 23: The process according to any preceding Paragraph wherein the bacterial strain is selected from the group consisting of *Bordetella pertussis*, *Neisseria meningitidis*, *Cornyebacterium diphtheriae*, *Clostridium tetani*, *Clostridium difficile*, *Helicobacter pylori*, *Haemophilus influenzae*, *Staphylococcus aureus*, *Streptococcus pneumoniae*, *Salmonella* species, *Spirochetes* species, *Legionella* species and *Mycobacterium tuberculosis*.

Paragraph 24: The process according to Paragraph 23 wherein the bacterial strain is selected from the group consisting of *Neisseria* meningitidisserogroup A, *Neisseria meningitidis* serogroup B, *Neisseria* meningitidisserogroup C, *Neisseria* meningitidisserogroup W135 and *Neisseria meningitidis* serogroup Y.

Paragraph 25: The process according to Paragraph 24 wherein the bacterial strain is *Neisseria* meningitidisserogroup B.

Paragraph 26: The process according to any preceding Paragraph wherein acetate levels in the culture medium remain below 4, below 3, below 2, below 1 or below 0.5 g/L throughout step c).

Paragraph 27: The process according to any preceding Paragraph wherein acetate levels in the culture medium are below 4, below 3, below 2, below 1 or below 0.5 g/L after at least 5, at least 7, at least 10, at least 12 or at least 15 hours of step c).

Paragraph 28: The process according to any preceding Paragraph wherein ethanol levels in the culture medium remain below 0.6, below 0.5, below 0.4, below 0.2 or below 0.1 g/L throughout step c).

Paragraph 29: The process according to any preceding Paragraph wherein ethanol levels in the culture medium are below 0.6, below 0.5, below 0.4, below 0.2 or below 0.1 g/L after at least 5, at least 7, at least 10, at least 12 or at least 15 hours of step c). Paragraph 30: The process according to any of the preceding Paragraphs wherein the pressure is reduced when the dissolved oxygen reaches its regulation setpoint or at a point in time thereafter.

Paragraph 31: The process according to Paragraph 30 wherein the pressure is reduced from 1.5 to 2 fold when the dissolved oxygen reaches its regulation setpoint, for example, reduced from 0.5 to 0.3 bar.

Paragraph 32: The process according to Paragraph 23 wherein the bacterial strain is a strain of *Streptococcus pneumoniae*.

Paragraph 33: The process of Paragraph 32 wherein the bacterial strain is *Streptococcus pneumoniae* serotype 1, 4, 5, 6A, 6B, 7F, 9V, 12F, 14, 15C, 33F, 18C, 19A, 19F, 22F or 23.

Paragraph 34: The process according to Paragraph 32 or 33 wherein lactate levels in the culture medium are below 30, below 25, below 20, below 15 or below 10 g/L throughout step c).

Paragraph 35: The process according to Paragraph 32 or 33 wherein lactate levels in the culture medium are below 30, below 25, below 20, below 15 or below 10 g/L after at least 1, at least 2, at least 3, at least 4 or at least 5 hours of step c).

Paragraph 36: A culture of bacteria in a fermenter having an optical density of at least 15, at least 20, at least 30, at least 40, at least 50, at least 60, or at least 70 units measured at 650 nm.

Paragraph 37: A culture of bacteria according to Paragraph 36 wherein the culture is a culture of a fastidious bacterial strain Paragraph 38: The culture of Paragraph 36 or 37 wherein the bacterial strain is selected from the group consisting of *Bordetella pertussis, Neisseria meningitidis, Cornyebacterium diphtheriae, Clostridium tetani, Clostridium difficile, Helicobacter pylori, Haemophilus influenzae, Staphylococcus aureus, Streptococcus pneumoniae, Salmonella* species, *Spirochetes* species, *Legionella* species and *Mycobacterium tuberculosis*.

Paragraph 39: The culture of Paragraph 38 wherein the bacterial strain is selected from the group consisting of *Neisseria* meningitidisserogroup A, *Neisseria* meningitidisserogroup B, *Neisseria* meningitidisserogroup C, *Neisseria* meningitidisserogroup W135 and *Neisseria* meningitidisserogroup Y.

Paragraph 38: The culture of Paragraph 39 wherein the bacterial strain is *Neisseria* meningitidisserogroup B Paragraph 39: The culture of Paragraph 38 wherein the bacterial strain is a strain of *Streptococcus pneumoniae*.

Paragraph 40: The culture of Paragraph 39 wherein the bacterial strain is *Streptococcus pneumoniae* serotype 1, 4, 5, 6A, 6B, 7F, 9V, 12F, 14, 15C, 33F, 18C, 19A, 19F, 22F or 23.

Paragraph 41: A process for producing a biopolymer or an aggregate of biopolymers including the steps of i) culturing a bacterial strain according to the process of the invention and ii) harvesting the biopolymer or aggregate thereof from the culture medium or filtrate.

Paragraph 42: The process according to Paragraph 41 wherein the bacterial strain is an outer membrane vesicle producing strain of Gram negative bacteria.

Paragraph 43: The process according to Paragraph 41, wherein the bacterial strain is from *Neisseria meningitidis*, optionally from serogroup B.

Paragraph 44: The process according to any one of Paragraphs 41-43 wherein the biopolymer or aggregate thereof is a protein.

Paragraph 45: The process according to any one of Paragraphs 41-43 wherein the biopolymer or aggregate thereof is an outer membrane vesicle.

Paragraph 46: The process according to Paragraph 41 wherein the bacterial strain is from *Neisseria* meningitidisserogroup A, C, W135 or Y.

Paragraph 47: The process according to Paragraph 46, wherein the biopolymer is a capsular polysaccharide.

Paragraph 48: The process according to Paragraph 41 wherein the bacterial strain is from *Bordetella*.

Paragraph 49: The process according to Paragraph 48 wherein the biopolymer or aggregate thereof is a protein, optionally pertussis toxin, 69 kDa pertactin or filamentous hemagglutinin.

Paragraph 50: The process according to Paragraph 41 wherein the bacterial strain is a strain of *Streptococcus pneumoniae*.

Paragraph 51: The process according to Paragraph 50 wherein the bacterial strain is *Streptococcus pneumoniae* serotype 1, 4, 5, 6A, 6B, 7F, 9V, 12F, 14, 15C, 33F, 18C, 19A, 19F, 22F or 23.

Paragraph 52: The process of according to Paragraph 51 wherein the biopolymer or aggregate thereof is capsular polysaccharide.

Paragraph 53: The process according to Paragraph 51 wherein the biopolymer or aggregate thereof is a protein such as pneumolysin, or a pneumococcal histidine triad protein.

Paragraph 54: The process according to any one of Paragraphs 51-53 comprising a further step of conjugating the biopolymer or aggregate thereof to a saccharide.

Paragraph 55: A process for producing a biopolymer or aggregrate thereof according to any one of Paragraphs 51-53 which comprises the further step of conjugating the biopolymer or aggregate to a camer protein.

Paragraph 56: A biopolymer or aggregate of biopolymers obtained or obtainable by the process of any one of Paragraphs 41-55.

Paragraph 57: A process for producing a vaccine comprising the steps of 1) producing a biopolymer or aggregate thereof using the process of any one of Paragraphs 41-55 and 2) formulating the biopolymer or aggregate thereof as a vaccine by adding a pharmaceutically-acceptable excipient and optionally further antigens and/or adjuvants.

DEFINITIONS

"Perfusion culture", also termed "perfusion suspension culture" herein, has its conventional meaning in the art, that is, it means that during culturing, cells are retained by a separation device in which there is an outflow of liquid having a lower cell density than prior to separation and in which there is an inflow of the growth medium.

"Tangential flow" in the context of flow filtration is a form wherein the majority of the feed flow travels tangentially across the surface of the filter, rather than into the filter.

Tangential-flow filtration is different from dead-end filtration in which the feed flow is passed through a membrane or bed, the solids being trapped in the filter and the filtrate being released at the other end.

"Alternating tangential flow" is a form of tangential flow wherein the direction of the tangential flow alternates between or among different directions.

A "fermenter" is any apparatus suitable for the industrial production of bacterial cultures. However this term does not include culture flasks which are typically used for growth of bacteria on a smaller scale.

The term "inhibitory metabolites" includes any chemical, biochemical compound or biopolymer that accumulates in the culture which may become inhibitory for growth of a microorganism of interest or for the production of a molecule of interest.

The term "fastidious bacteria" is used herein according to its standard meaning in bacteriology, i.e. to refer to bacteria having complex nutritional requirements.

"Biopolymers" are polymers produced by living organisms, which include proteins, polysaccharide and polynucleotides, as well as for example bacterial toxins or toxoids or other bacterial polymers that can be used as an antigen in a vaccine. The biopolymers may be naturally produced by the organism or the organism may be genetically engineered to produce the biopolymer recombinantly. Proteins may be produced from an expression cassette comprising their native or a heterologous promoter.

An "aggregate of biopolymers" refers to multiple associated, e.g. non-covalently associated, biopolymers (of the same type or different types) and includes, for example, outer membrane vesicles, microvesicles, outer membrane complexes (OMPC) blebs and the like. WO02/062378 describes suitable methods and bacterial strains for increasing bleb production, if required.

The term "suspension culture" when used herein has its normal meaning in the art, i.e. typically a culture wherein single cells and small cell aggregates are grown in a liquid growth medium that is kept agitated by means of bubbling, shaking, or stirring so the cells do not settle out.

The terms "comprising", "comprise" and "comprises" herein are intended to be optionally substitutable with the terms "consisting of", "consist of" and "consists of", respectively, in every instance.

BRIEF DESCRIPTION OF THE FIGURES

FIG. 3 shows a typical *N. meningitidis* fermentation profile ATF with pO2/substrate regulation (Agitation speed (rpm) and dissolved oxygen (%) over time.

FIG. 4 shows a typical *N. meningitidis* fermentation profile ATF with pO2/substrate regulation (Acid consumption (grams) or base consumption (grams) over time.

FIG. 5 shows a typical *N. meningitidis* fermentation profile ATF with pO2/substrate regulation (Temperature (° C.) and Head Pressure (bar) and pH).

FIGS. 6, 7 and 8 show typical N. *Meningitides* fermentation profiles with the process parameters monitored during 20 L-scale fermentation where pre-determined perfusion rates are applied, as in Example 2.

FIG. 6 shows a typical *N. meningitidis* fermentation profile ATF with constant perfusion rate (Agitation speed (rpm) and dissolved oxygen (%) over time.

FIG. 7 shows a typical *N. meningitidis* fermentation profile ATF with constant perfusion rate (Acid consumption (grams) and base consumption (grams)) over time.

FIG. 8 shows a typical *N. meningitidis* fermentation profile ATF with constant perfusion rate (Temperature (° C.) and Head Pressure (bar) and pH).

FIG. 9 is a process flowsheet for batch mode fermentation of *N. meningitidis*.

FIG. 10 is a process flowsheet for perfusion mode fermentation of *N. meningitidis*.

FIG. 11 shows a fermentation profile over time of *Streptococcus pneumoniae* serotype 22F with ATF with the process parameters monitored during 20 L-scale perfusion fermentation as in Example 3.

FIG. 12 shows the accumulation of polysaccharide in the different fractions (permeate and culture) over time from *Streptococcus pneumoniae* serotype 22F culture with ATF as in Example 3.

FIG. 13 shows the evolution of glucose and lactate concentration in the culture over time from *Streptococcus pneumoniae* serotype 22F culture with ATF as in Example 3.

DETAILED DESCRIPTION

Referring to FIG. 1 there is shown a fluid filtration system comprising a perfusion fermenter 1 which is connected to a housing assembly 2, containing a hollow-fibre filtration module. The housing assembly 2 is positioned between the fermenter 1 and a diaphragm pump 3, controlled by an an alternating tangential flow controller (ATF) 4. A filtrate pump 5, such as a double headed peristaltic pump, (e.g. a Watson Marlow 505U) is used for controlled addition of the feeding medium from inlet 6 and removal of the filtered stream (exhaust medium) by an outlet 7. The rate of the filtrate pump 5 may be automatically controlled by an online measurement performed by a sensor such as a pO2 probe 11 through a pump controller 12. Unfiltered material remains in the system.

The diaphragm pump 3 provides the means for generating alternating tangential flow between fermenter 1 and filtrate pump 5, through the hollow fibres, thus generating rapid, low shear, tangential flow. The diaphragm pump is partitioned into two chambers with a flexible diaphragm. The first pump chamber serves as a liquid reservoir that registers with the fermenter through the fibre module. The second pump chamber is an air chamber that registers with the pump flow control system. In FIG. 1 (Phase 1, Pressurisation), controlled addition of compressed air from the air inlet 8 via the air filter 9 into the system increases the pressure in the second pump chamber (air chamber) relative to the fermenter. This expands the air chamber, inversely reducing the volume in the first pump chamber (liquid reservoir), driving the liquid content away from the diaphragm pump, through the hollow fibre module and to the fermenter, thus generating tangential flow in one direction.

Referring to FIG. 2 there is shown the fluid filtration system of FIG. 1 in exhaust phase. In FIG. 2 (Phase 2, Exhaust), the pressure in the air chamber is reduced by removal of compressed air from the air outlet 10 and so is reduced relative to the pressure in the fermenter, and liquid flows from the fermenter to the liquid reservoir of the pump. The filtered stream (exhaust medium) is removed by outlet 7 generating tangential flow in the other direction. This movement is helped by fermenter overpressure (0.5 to 0.1 bar).

In order that this invention may be better understood, the following examples are set forth. These examples are for purposes of illustration only, and are not to be construed as limiting the scope of the invention in any manner.

EXAMPLES

Example 1

Example 1 describes a process for growing *Neisseria meningitidis* in perfusion culture using ATF. Example 1(a) describes a process for making a solid pre-culture of *N. meningitidis*, Example 1(b) describes a process for making a liquid pre-culture of *N. meningitidis*, and Example 1(c)

describes a perfusion culture using ATF initiated with a liquid pre-culture of *N. meningitides* as starting material.

Example 1 (a) *Neisseria meningitidis* B2486 Solid Pre-Culture

A solid pre-culture was prepared using a frozen seed culture of *Neisseria meningitidis* serotype B strain H44/76 (MenB). The seed culturability was determined by plating serial dilutions of the seed, as approximately $5\times10^8$ colony forming units per ml.

The seed culture was thawed to room temperature and 100 μl were used to inoculate a solid pre-culture (Agar plate) containing 15 ml of pre-culture agar medium derived from Frantz (J. Bact. 43(6): 757-761 (1942)).

The inoculated Agar plate was then incubated at 36° C. (±1° C.) in an environment regulated at 5% of $CO_2$ and saturated in humidity, for 23 h (±2 h). One $40^{th}$ of the resuspended cells was used to inoculate the second pre-culture step (liquid pre-culture) (Example 1 (b)).

Example 1 (b) *Neisseria meningitidis* B2486 Liquid Pre-Culture

The entire cell layer grown on the solid pre-culture (as described in Example 1(a)) was resuspended in 8 ml (±1 mL) of liquid pre-culture medium derived from Frantz (J. Bact. 43(6): 757-761 (1942)), containing 20 g/L glucose, 1.5 g/L $NaH_2PO_4.2H_2O$, 40 g/L soy peptone and 4 g/L sodium glutamate. A volume of 0.5 ml (±0.1 ml) of this suspension was diluted in 4.5 ml of NaCl 0.9%. A volume of 2.0 ml of this dilution was used to inoculate a 2 L Erlenmeyer shake flask containing 400 ml of pre-culture medium.

The inoculated flasks were then incubated at 36° C. (±1° C.) and 200 rpm. The pre-cultures were stopped when the optical density at 650 nm ($OD_{65onm}$) reached at least 3.0, (around 15 h±2 h of incubation). The pre-culture was used to inoculate medium in a fermenter as soon as practical after the culture was stopped (Example 1 (c)).

Example 1(c) 20 L Scale ATF Perfused Fermentation of *N, Meningitidis* Using a Perfusion Rate Regulated by the Oxygen Demand A 20-liter fermenter (Biolafitte) was used. The vessel was equipped with an Alternating Tangential Flow 4 device (ATF4 from Refine Technology). The ATF was set up with a 0.2 μm filter (GE Healthcare—CFP-2-E-8SIP) and the whole system was sterilized by autoclaving prior to being assembled to the fermenter. 13 liters of fermentation medium (a similar medium as in Example 1(b), but containing only 5 g/L glucose) were aseptically transferred into the fermenter. (If necessary, the pH of the medium may at this point be readjusted to 7.0 with base addition.) One ml of undiluted irradiated antifoam (SAG 471) was added to the fermenter. The temperature (36° C.), head pressure (0.5 bar), aeration rate (20 liters sparged air per minute) and initial agitation (stirring) speed (100 rpm) were then set prior to inoculation. The level of dissolved oxygen in these conditions was defined as 100%.

The aeration rate was maintained at a constant level during the fermentation. pH was controlled at 7.0 by an acid/base regulation ($H_3PO_4$ 25%/NaOH 5N) throughout the fermentation.

Inoculation was achieved by the addition of 800 ml of liquid pre-culture (prepared from two Erlenmeyer shake flasks, as described in Example 1(b)).

The fermentation process consisted of 3 phases: a first phase (the "pre-perfusion phase") where glucose is not limiting the growth rate and there is no perfusion, a second phase (perfusion phase 1) where glucose is not limiting, but perfusion has been initiated and a third phase (perfusion phase 2) wherein glucose is limiting the growth rate and perfusion is taking place.

During the first phase (pre-perfusion), the temperature was maintained at 36° C., pH was maintained at 7.0, head pressure was maintained at 0.5 bar, and aeration was maintained at 20 liters per minute. The level of dissolved oxygen (DO) was set at 20%. The level of DO was regulated by increasing stirring when the DO fell below 20%. After 2.6 hours (when dissolved oxygen is regulated at its setpoint (20%) by stirring), perfusion was started, thus starting the second phase (perfusion phase 1).

In perfusion phase 1, the head pressure was decreased from 0.5 to 0.3 bar.

Temperature was maintained at 36° C., pH was maintained at 7.0, aeration was maintained at 20 liters per minute. A double head peristaltic pump was used for both feeding fresh growth medium (similar to in Example 1(b), but containing 10 g/L glucose) into the bioreactor and extracting filtrate from ATF at a similar flow rate of 3.5 L/h (perfusion rate), in order to minimize fermentation volume fluctuations due to perfusion. The ATF rate (the volume of media passing from the fermenter to the ATF device through the filter and vice versa per time unit) was set at 3.5 L/min (Pressurisation flow=Exhaust flow), pressure and exhaust delays were automatically adapted by the system to reach that value.

After 7 hours, (as soon as glucose was becoming limiting for growth), the fermentation went into the third phase (perfusion phase 2) wherein the temperature was decreased to 31.5° C. and the perfusion rate was gradually decreased to 1.5 L/h. Then, the perfusion rate was automatically controlled by oxygen demand (pO2/substrate regulation), decreasing perfusion rate when dissolved oxygen dropped below about 20% and increasing it in the opposite case. At this point the agitation speed was maintained at approximately 700 rpm to ensure a constant and non-limiting oxygen supply. The ATF rate was then increased to 5.0 L/min. Head pressure was maintained at 0.3 bar, pH was maintained at 7.0, aeration was maintained at 20 liters per minute.

During this third phase, temperature was regulated at 31.5° C. and the ATF rate was increased from 5.0 to 7.0 L/min in parallel of biomass increase. At the end of fermentation (24 h), cell paste was collected by centrifugation (5000×g, 4° C. for 30 min), and stored at −20° C.

At the end of fermentation (24 h), the following biomass levels were determined:

TABLE 1

| Final OD650 nm | Dry Cell Weight | Wet Cell Weight |
|---|---|---|
| 75.7 (10 L) or 58.2* | 57.7 g/L (10 L) or 44.4 g/l* | 270 g/L (10 L) or 207.7 g/l* |

*Values calculated for starting medium volume of 13 L

Example 2 20 L Scale ATF Perfused Fermentation of *N, Meningitides* Using Pre-Determined Perfusion Rates Fermentation conditions were equivalent to those described in Example 1 except that:

1) Culture medium contained 10 g/L glucose.

2) After 3.3 h of culture (when dissolved oxygen was regulated at its set point (20%) by stirring), fermentation medium was added in a perfusion mode through the ATF device at a rate of 3.5 L/h; after 6.5 h of culture, the head pressure was decreased from 0.5 to 0.3 bar.

3) at 9.5 h of culture (when the $OD_{650\ nm}$ reached approximately 20) when glucose became limiting for growth rate, perfusion rate was decreased from 3.5 to 2.0 L/h and maintained at this setpoint throughout the third fermentation phase (perfusion phase 2). Dissolved oxygen was also regulated by the agitation speed during the whole fermentation. At the end of fermentation (24 h), the following biomass levels were determined:

TABLE 2

| Final OD650 nm |
|---|
| 54 (10 L) |

Figure 1:
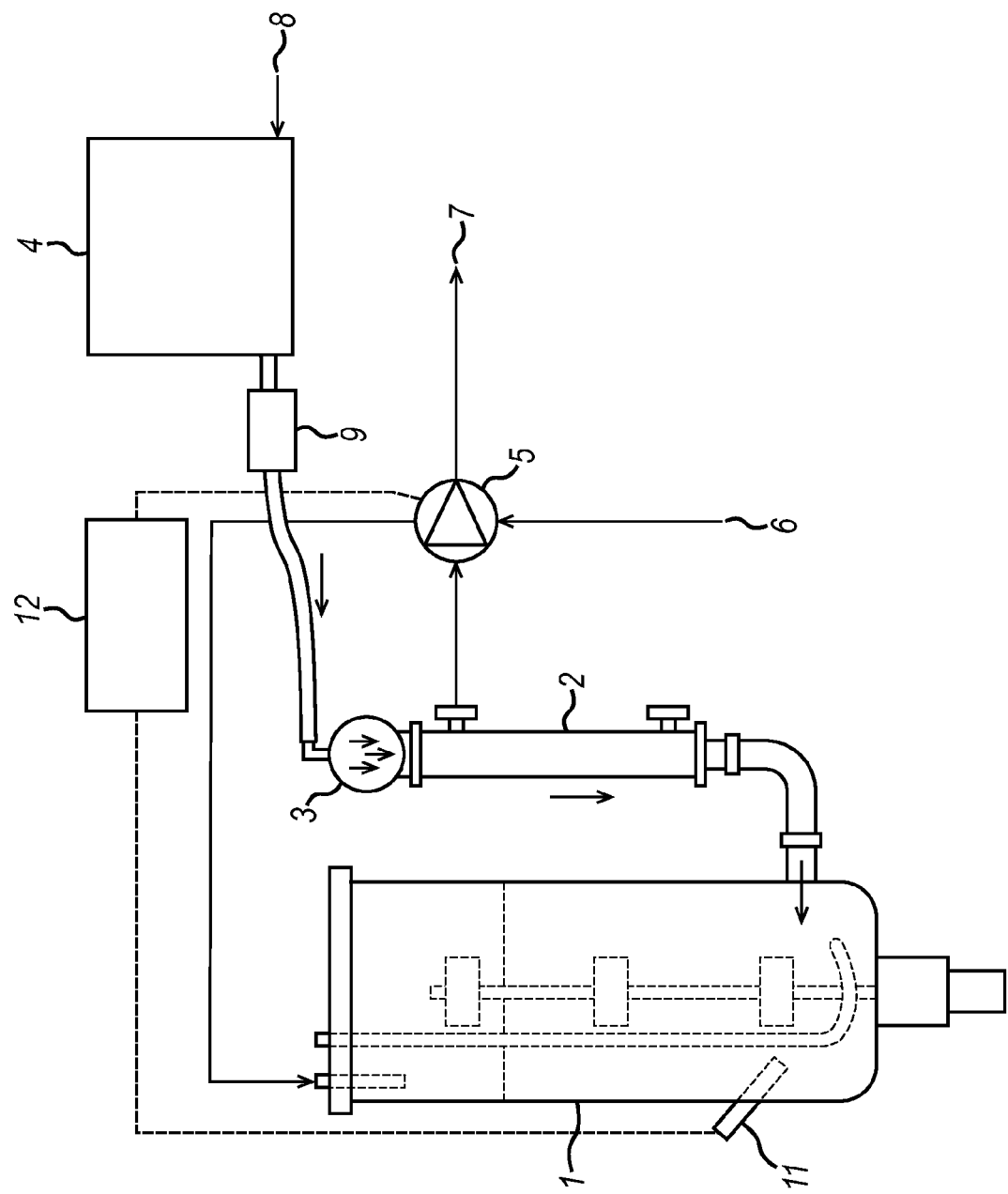
FIG. 1 shows a systematic representation of a fermentation system incorporating ATF showing the flow of the fermentation broth to a vessel through the ATF system upon pressurisation.
Figure 2:
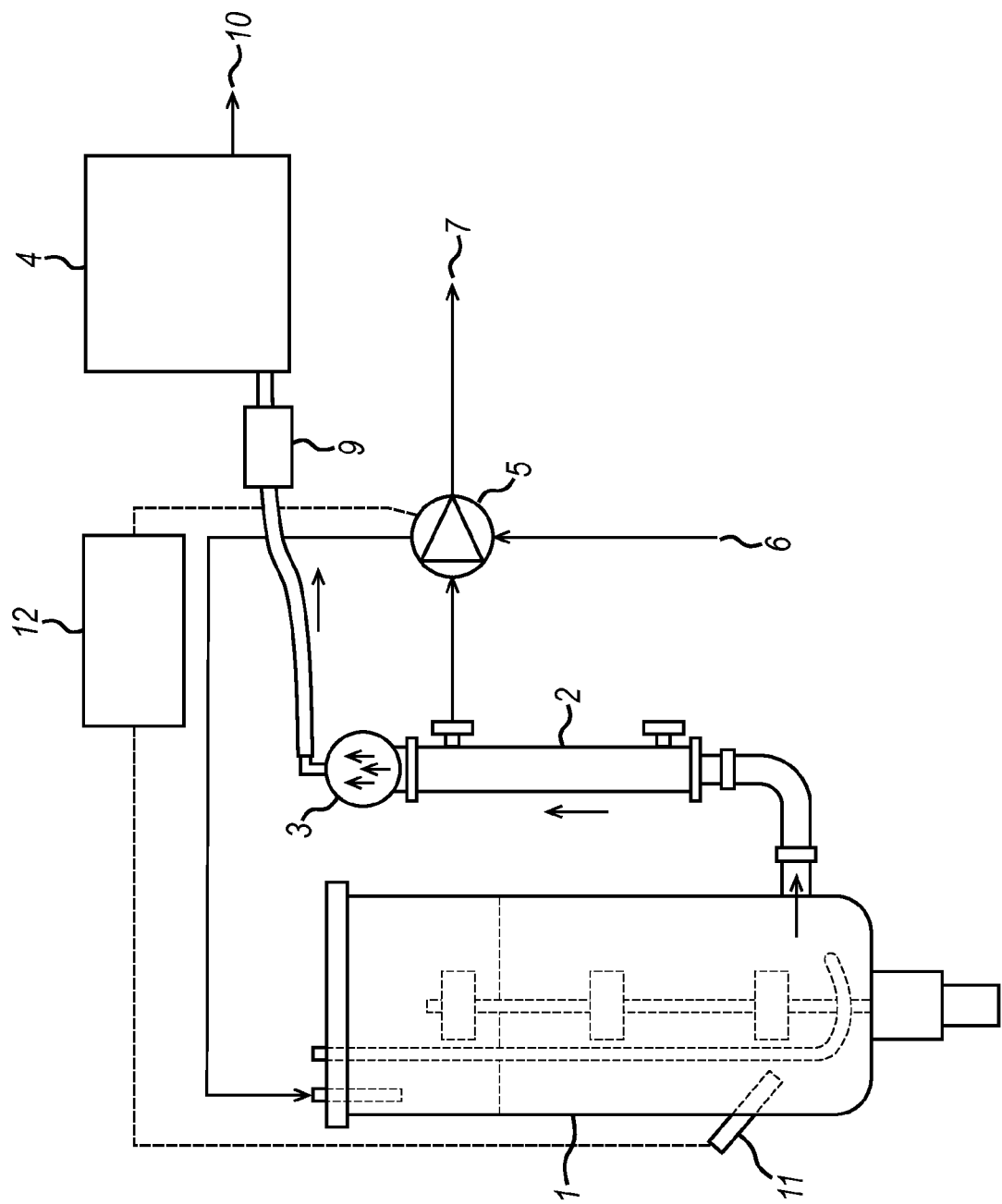
FIG. 2 shows a systematic representation of the fermentation system shown in FIG. 1 showing the flow of the fermentation broth from the vessel through the ATF system upon exhaust.
Figure 3:
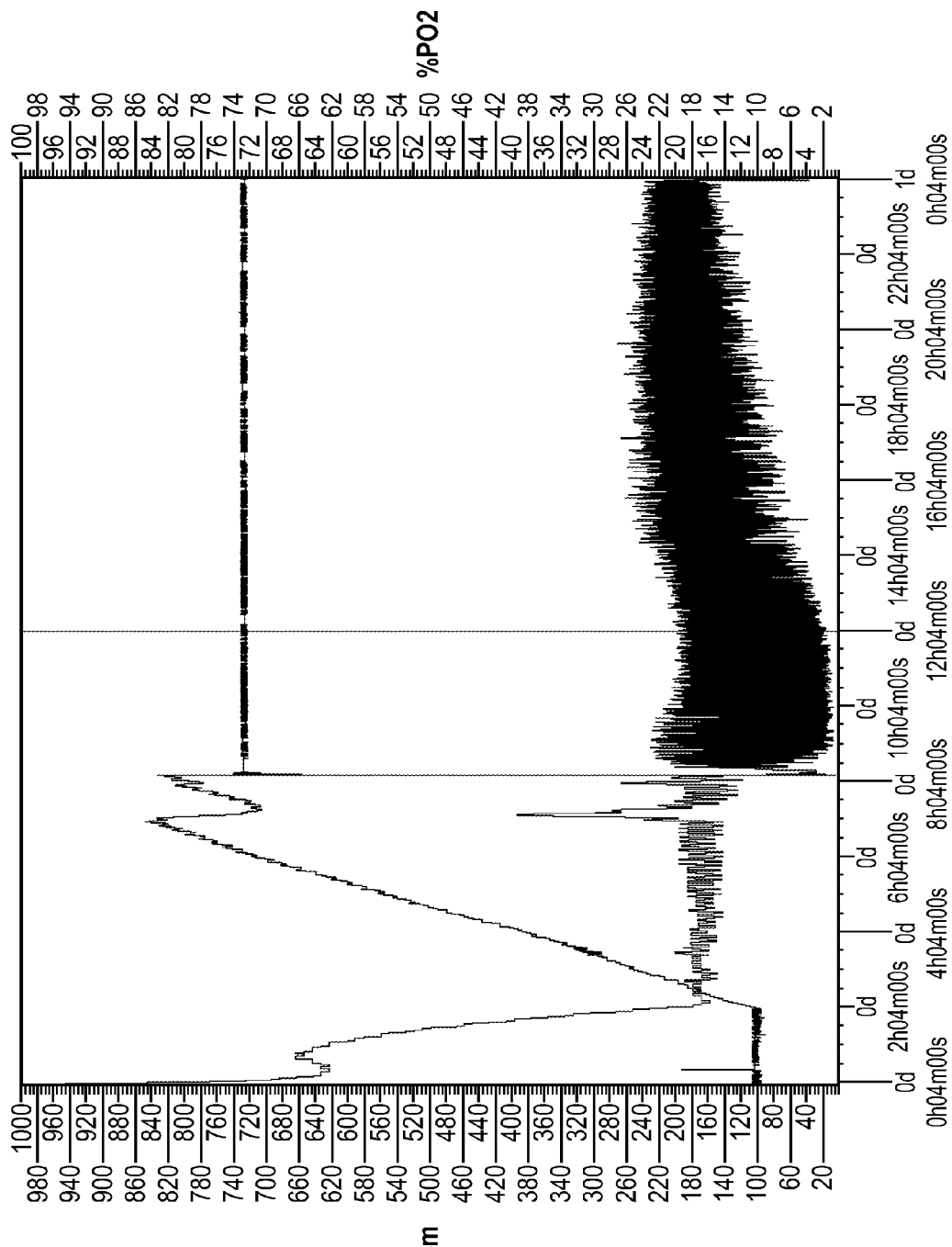
FIGS. 3, 4 and 5 show a typical *N. meningitidis* fermentation profile with the process parameters monitored during 20 L-scale perfusion fermentation when perfusion rate is mediated by oxygen demand as in Example 1.
Figure 4:
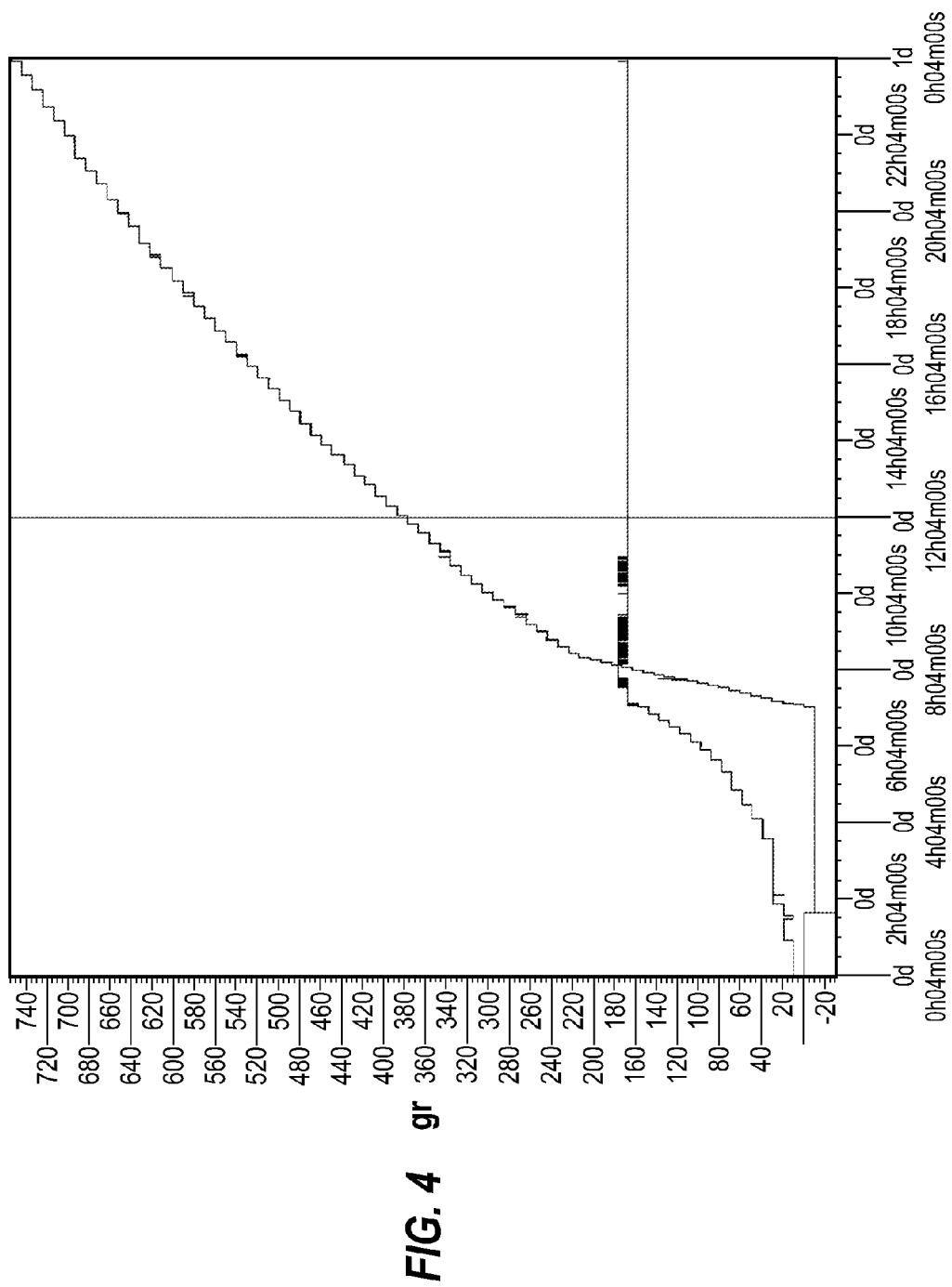
Figure 5:
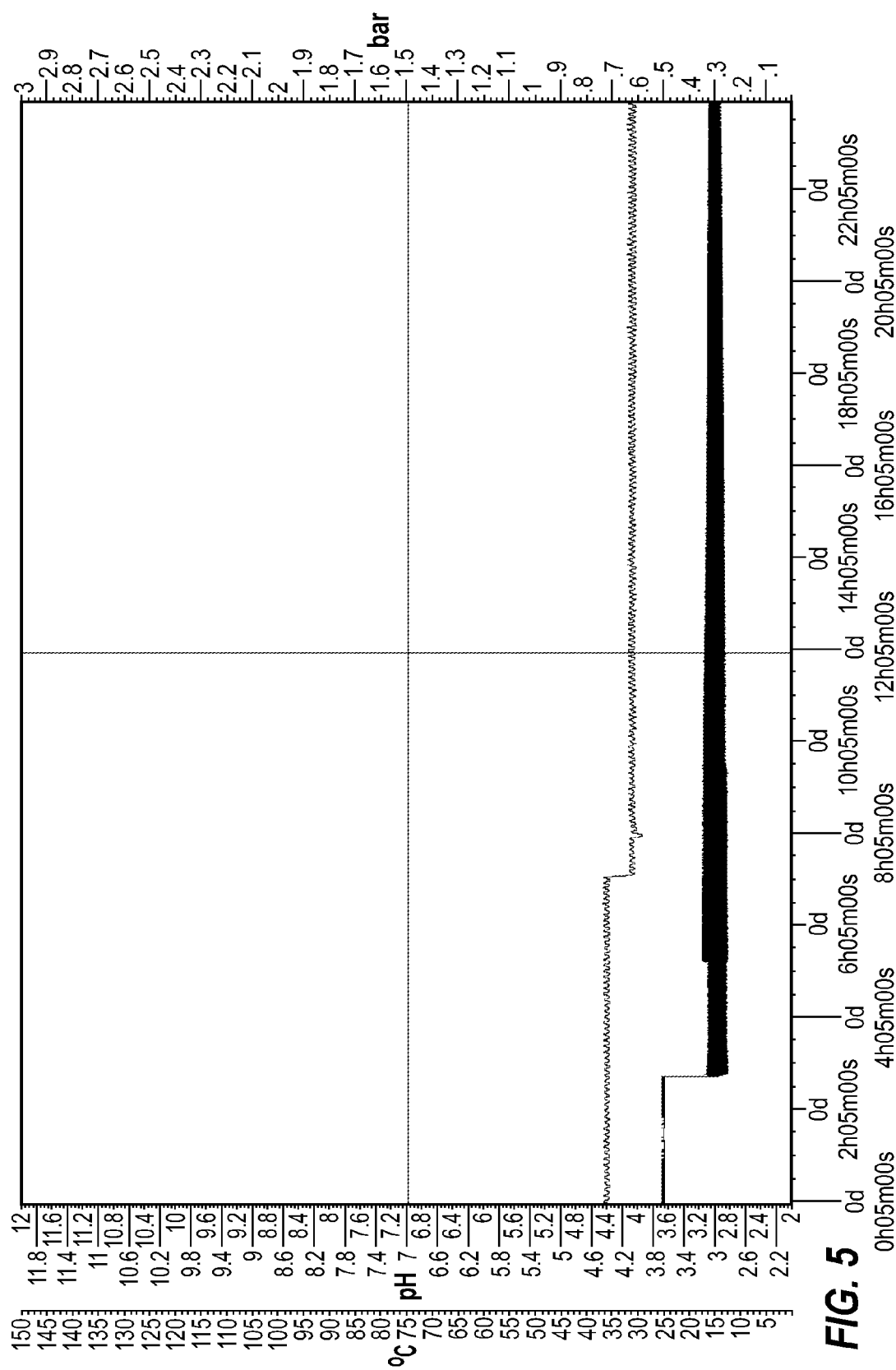
Figure 6:
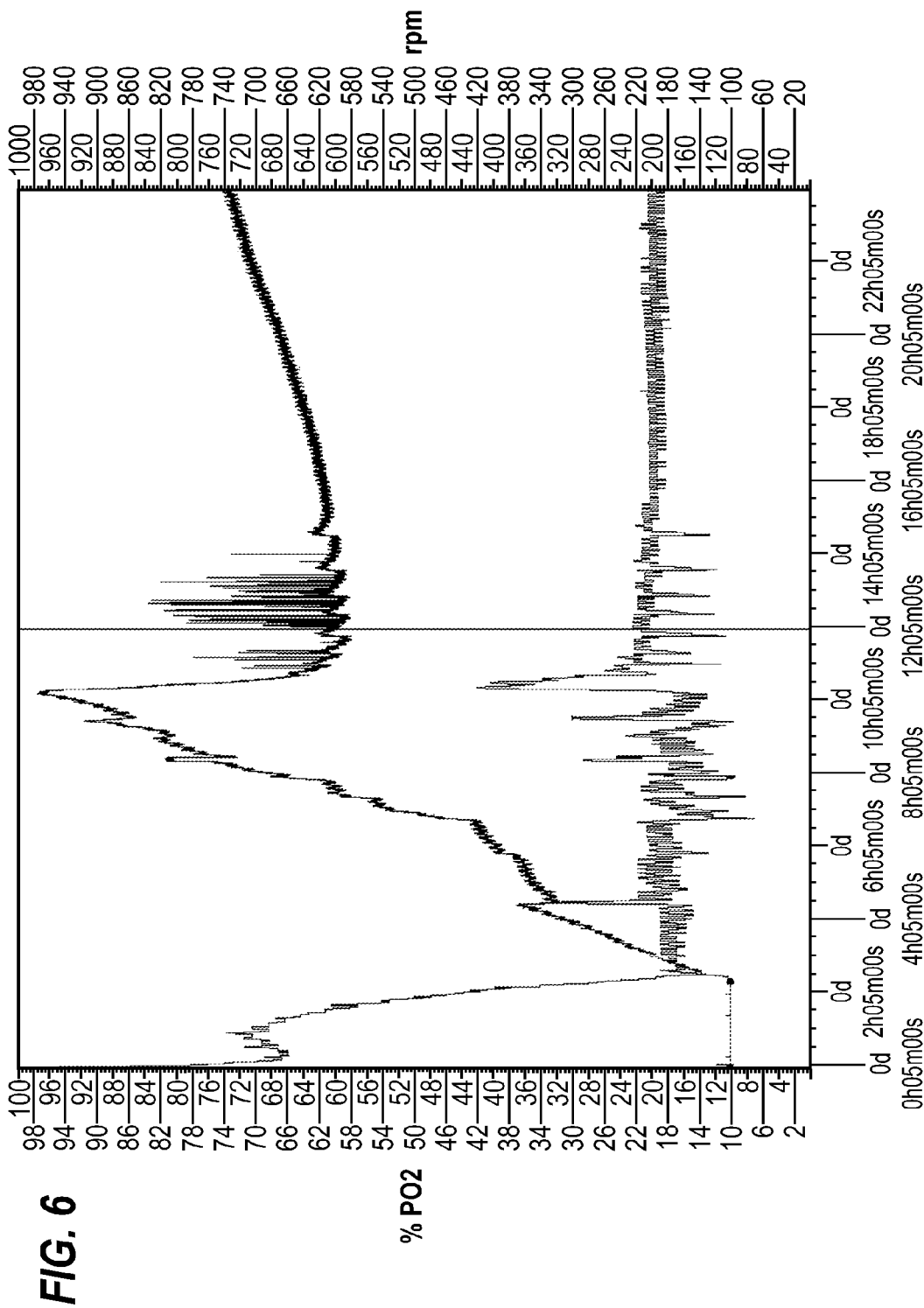
Figure 7:
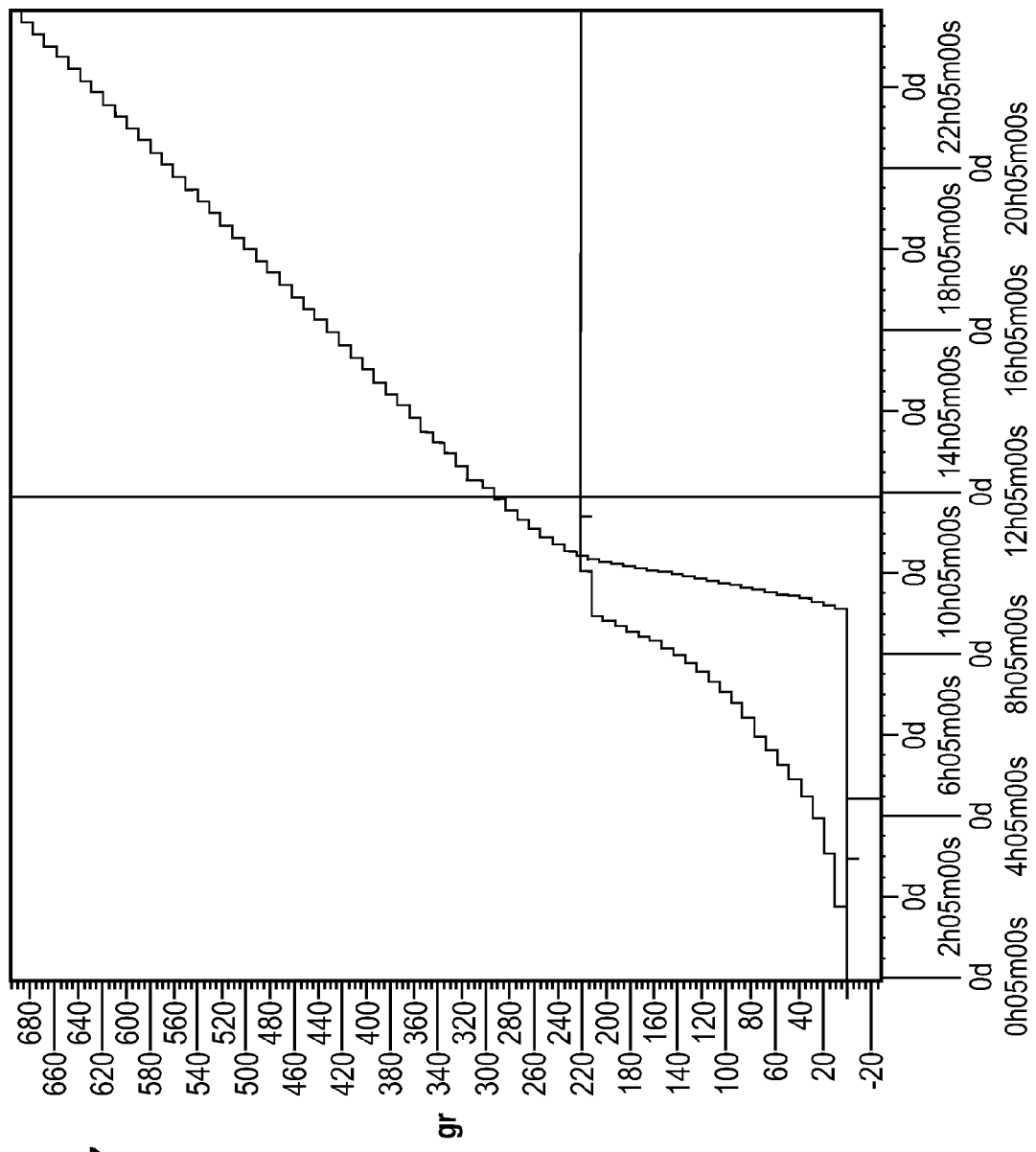
Figure 8:
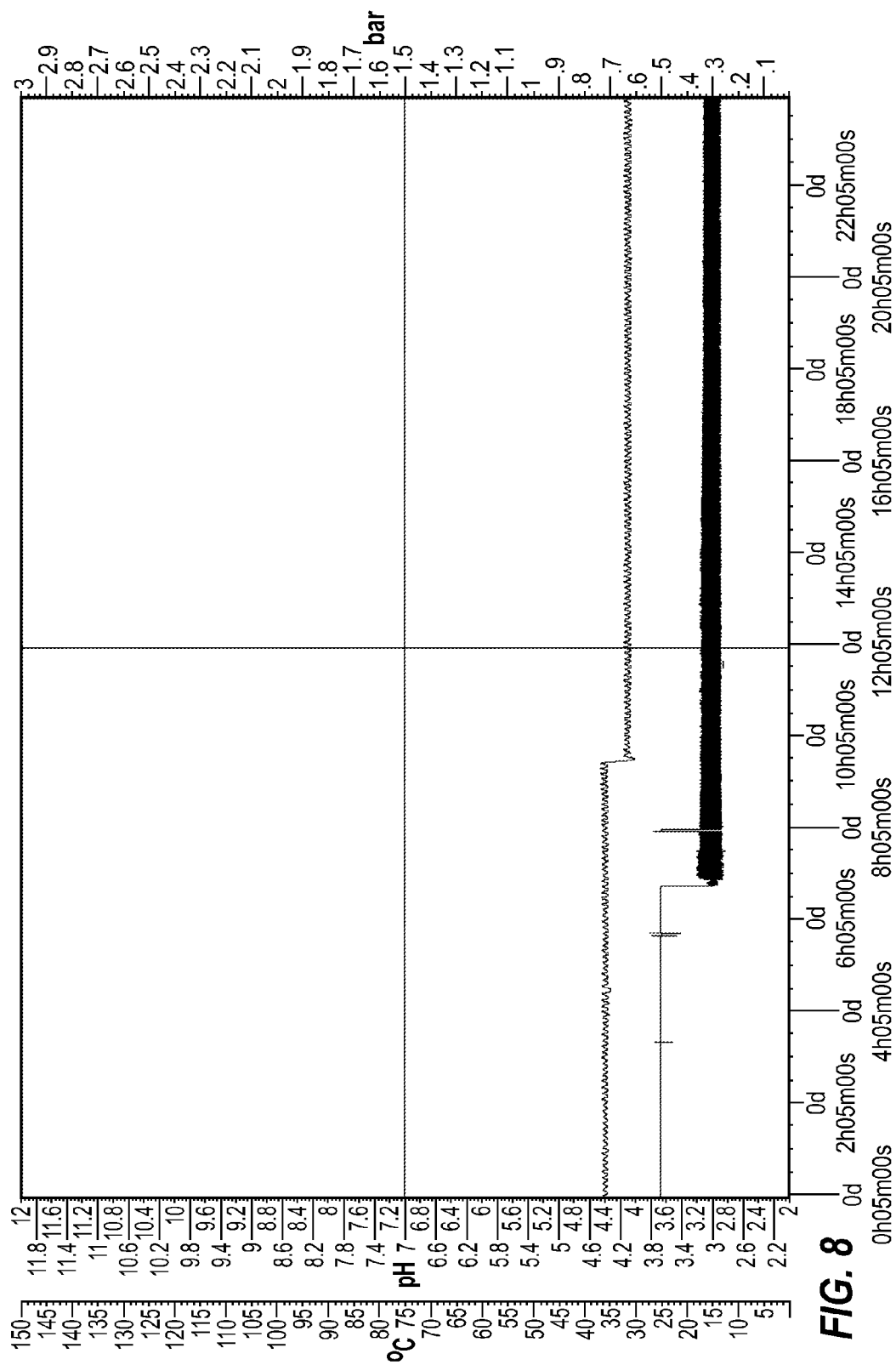
Figure 9:
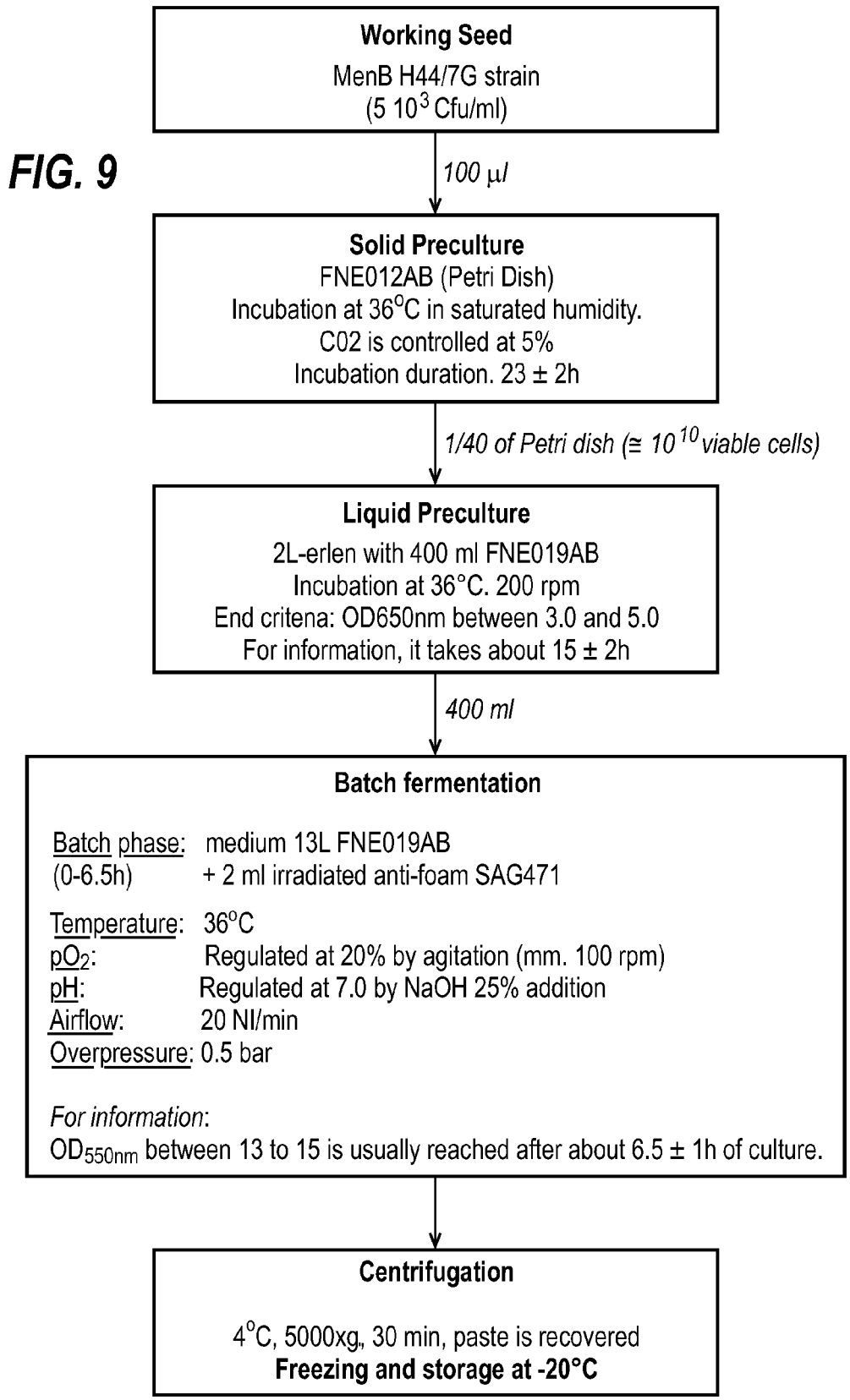
Figure 10:
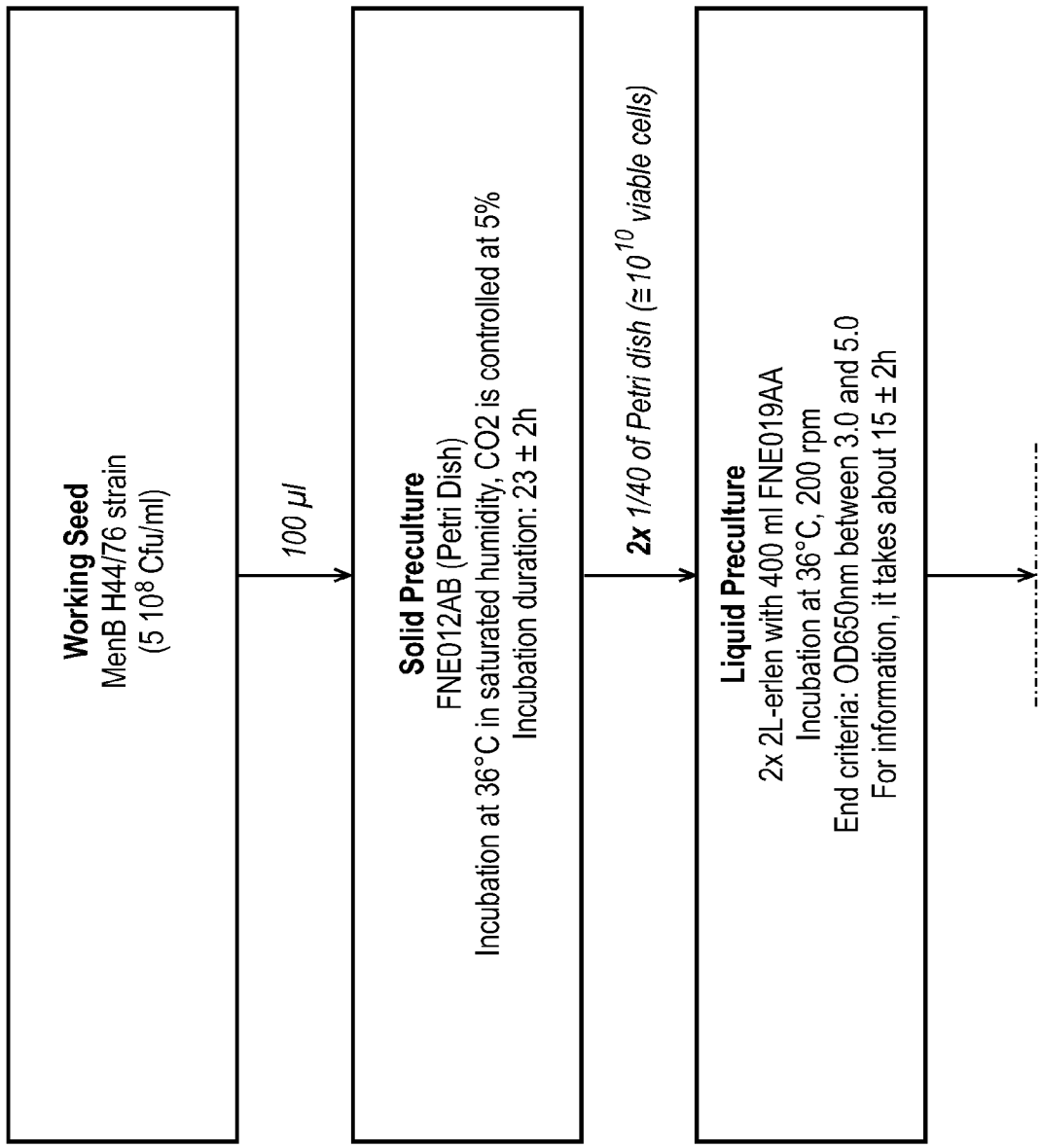
Figure 11:
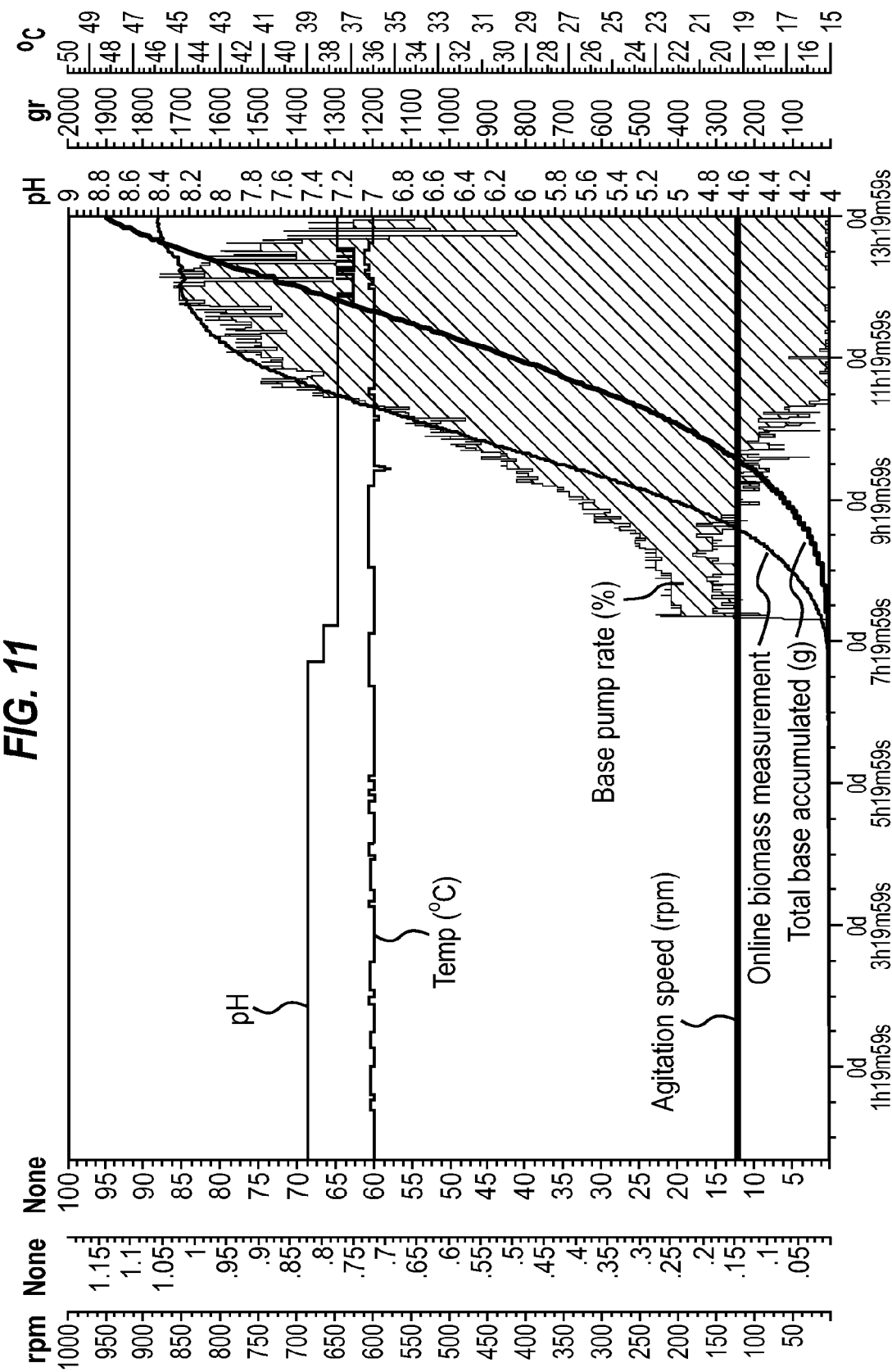
Figure 12:
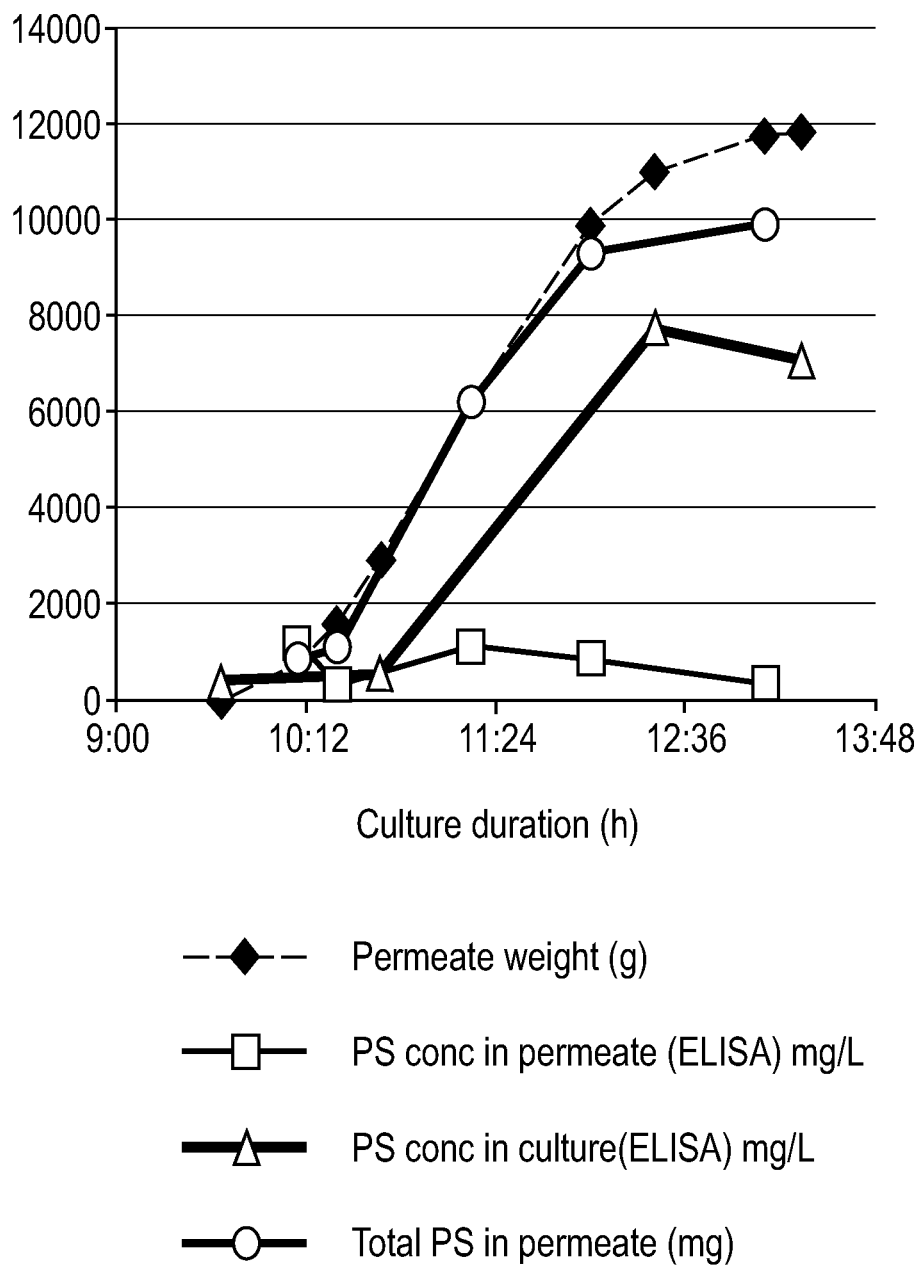
Figure 13:
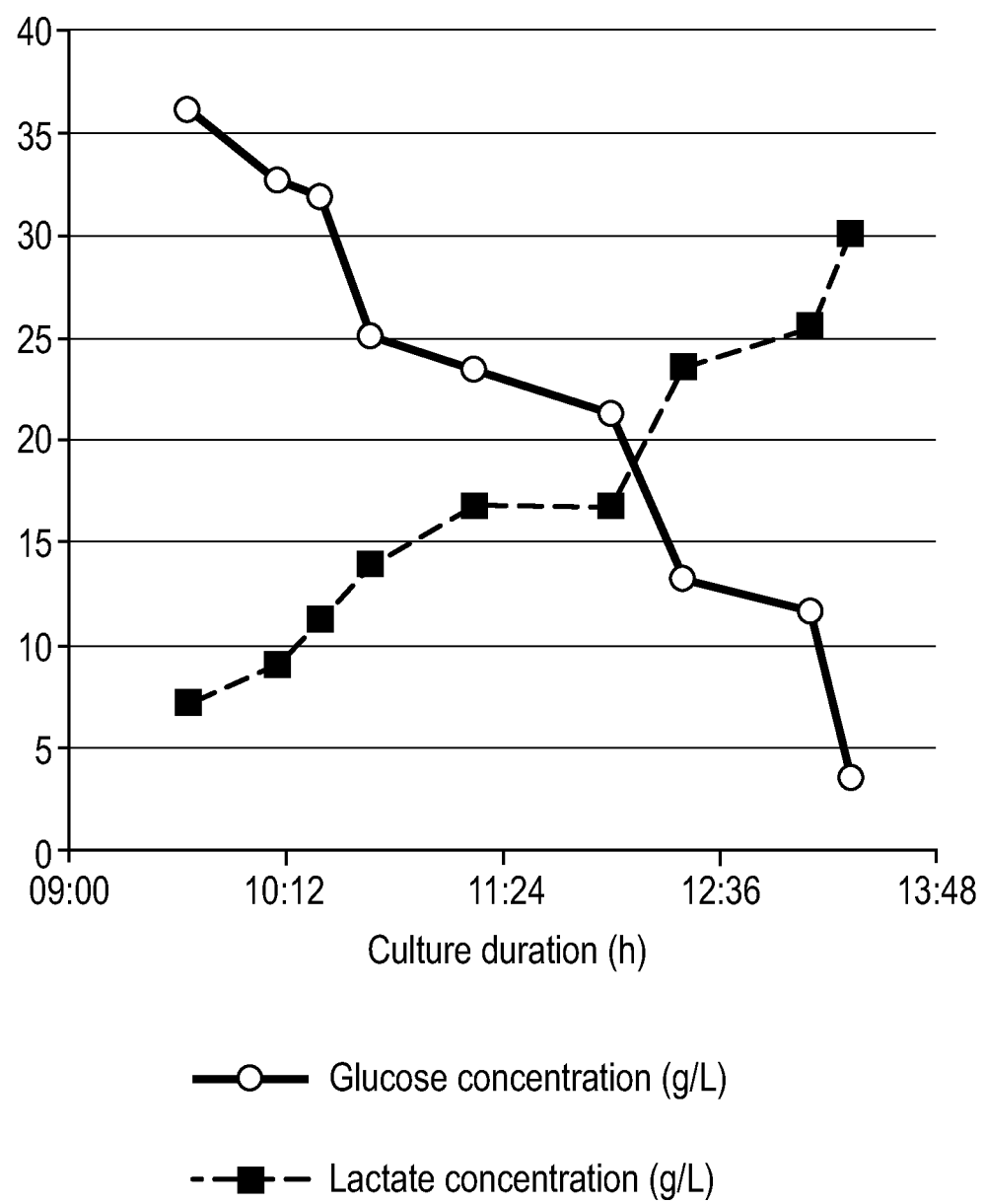

FIGS. 11 and 12 show respectively the batch and perfusion processes in the form of a flow sheet. The perfusion process is as described in Example 1(c).

Table 3 shows a comparison of the results of different fermentation modes, all using *N. meningitides*.

TABLE 3

|  | Batch mode | Fed-batch mode | Perfusion mode |
|---|---|---|---|
| Culture duration | 6.5 h | 8.5 h | 24 h |
| OD650 nm | 13.9 | 16.6 | 54-58.2 |
| Dry Cell Weight (DCW) | 8.7 g/L | — | 44.4 g/L |
| Wet Cell Weight (WCW) | 46.1 g/L | 51 g/l | 207.7 g/L |

As shown above, batch fermentation reached a maximal cell density of about 13.9.

Further growth may in principle be limited by two factors: the consumption of substrates present in the medium and the possible accumulation of one or more inhibitory metabolites leading cells to growth limitation and, finally, lysis.

Substrate limitation in batch mode cannot be avoided by simply increasing substrate concentrations in the medium, because an increased amount of substrate makes dissolved oxygen level impossible to maintain at a constant value (reach of a maximal agitation speed).

An alternative would be fed-batch fermentation, which can feed cells slowly in order to control oxygen supply. In this system, the feeding rate is controlled by the oxygen demand and agitation speed is maintained at a constant level. However, as can be seen in Table 3, fed-batch results revealed the same growth limitation as observed for batch mode with a maximal optical density obtained around 16. Cell lysis was observed at this point forward. This observation indicated that substrate is not the main limiting factor, but that possible accumulation of one or more inhibitory metabolites during the culture might inhibit further growth.

As shown above, the perfusion mode using the ATF device wherein cells were slowly supplied with substrate and, at the same time, spent medium was removed, gave a significant increase in yield.

Example 3 20 L Scale ATF Perfused Fermentation of *S. Pneumoniae* Using Pre-Determined Perfusion Rates A 20-liter fermenter (Biolafitte) was used. The vessel was equipped with an Alternating Tangential Flow 4 device (ATF4 from Refine Technology). The ATF was set up with a 0.2 µm filter (GE Healthcare—CFP-2-E-8SIP) and the whole system was sterilized by autoclaving prior to being assembled to the fermenter. A fermentation medium similar to that described in Hoeprich (1955) J Bacteriol 69(6): 682-688 was used with the modification that it contained 45 g/L rather than 12.5 g/L glucose and 200-400 mg/L Choline HCl). 10 liters of fermentation medium were aseptically transferred into the fermenter. (If necessary, the pH of the medium may at this point be readjusted to 7.2 with base addition.) The temperature (36° C.), head pressure (0.1 bar), aeration rate (2 liters air per minute in the headspace of the fermenter) and agitation (stirring) speed (100 rpm) were then set prior to inoculation. The aeration rate was maintained at a constant level during the fermentation as well as the stirring. pH was controlled at 7.2 by base addition (NaOH 5N) throughout the fermentation.

Inoculation was achieved by the injection of 40 µL of *Streptococcus pneumoniae* serotype 22F working seed suspension (the viability of the seed was estimated at $2.7\ 10^9$ colony forming units per ml) directly in the fermenter through a septum in the headplate.

The fermentation process consisted of in 3 phases: a first phase (the "pre-perfusion phase") where glucose is not limiting the growth rate and there is no perfusion, a second phase (perfusion phase) where glucose is not limiting, but perfusion has been initiated, and a third phase (post-perfusion phase) wherein the feeding is stopped but the ATF is still in action to extract permeate, and the culture is pursued in batch mode.

During the first phase (pre-perfusion), the growth is initiated. When the optical density (650 nm) reached 2.85 (9 h40' of culture), the second phase (perfusion phase) was started.

In the perfusion phase, all culture parameters were maintained constant. A double headed peristaltic pump was used for both feeding fresh growth medium (of the same composition as the initial medium) into the bioreactor, and extracting filtrate from ATF at a similar flow rate of 3 L/h (perfusion rate), in order to minimize fermentation volume fluctuations due to perfusion. Perfusion rate was maintained at 3 L/h for the first 45 min and then increased to 6 L/h. Alternating Tangential Flow (ATF) was set at a rate of 2.5 L/min for the first 95 min then at 10 L/h. During the perfusion phase, the rate of filtrate extraction progressively decreased while medium level in the fermenter increased (due to the constant feed rate). After 12 hours of culture, the feeding was stopped, while the permeate extraction was maintained (post-perfusion phase). The culture was continued, maintaining the process parameters constant until 13 h20' of culture.

Culture and permeate were sampled periodically in order to evaluate the polysaccharide content and accumulation.

FIG. 11 shows a fermentation profile with the process parameters monitored during 20 L-scale perfusion fermentation, FIG. 12 shows the accumulation of polysaccharide 22F in the different fractions (permeate and culture).

At the end of fermentation (13 h20), the following biomass and Polysaccharide 22F (ELISA assay) levels were determined

TABLE 4

| Culture duration (hh:mm) | With ATF | W/O ATF | Ratio with ATF/ without ATF |
|---|---|---|---|
| Experiment | SPC1521 | SPC1447 | |
| Final volume in fermenter (L) | 14 | 17.5 | |
| Fermentation duration (h) | 13:20 | 13:35 | |
| Max OD (650) | 12.1 | 7.8 | 1.55 |
| Permeate weight (g) | 11848 | NA | |

TABLE 4-continued

| Culture duration (hh:mm) | With ATF | W/O ATF | Ratio with ATF/ without ATF |
|---|---|---|---|
| PS conc in fermenter at end (mg/L) | 7057 | 2217 | 3.18 |
| Total PS in fermenter (mg) | 98798 | 38797 | 2.55 |
| Total PS in permeate (mg) | 9893 | NA | |
| Overal Total PS (mg) | 108691 | 38797 | 2.80 |
| Overal volume (L) | 25.85 | 17.5 | 1.48 |
| Overal PS productivity (mg/L) | 4205 | 2217 | 1.90 |

The invention claimed is:

1. A process for culturing a fastidious bacterial strain in a fermenter comprising the steps of:
   a) adding a liquid growth medium comprising a carbon source to a fermenter;
   b) seeding the growth medium with the fastidious bacteria to form a culture medium; and
   c) growing the fastidious bacteria in perfusion suspension culture, where an average perfusion rate is above 5% of culture volume per hour;
   wherein the culture medium including the bacteria is circulated over a separation system in alternating tangential flow, and the separation system removes a filtrate containing spent medium from the culture medium and retains the fastidious bacteria in the culture medium,
   d) reducing the perfusion rate of step c) when the carbon source in the medium is exhausted.

2. The process according to claim 1 wherein the spent medium contains inhibitory metabolites.

3. The process according to claim 1 wherein the separation system comprises a filter module comprising hollow fibre membranes for the removal of inhibitory metabolites from the culture medium.

4. The process according to claim 1 wherein in step c) the average perfusion rate is 10% or above of the culture volume per hour.

5. The process according to claim 1 wherein the perfusion rate in step c) is reduced 1.5 or 2 fold when the carbon source in the medium is exhausted.

6. The process according to claim 1 wherein in step c) the dissolved oxygen level is kept at between 10% and 30% of the initial level.

7. The process according to claim 1 wherein the suspension culture has a volume selected from at least 10 liters, at least 20 liters, at least 50 liters, at least 100 liters, and at least 250 liters.

8. The process according to claim 1 wherein the density of the bacteria reaches at least 10 OD units measured at 650 nm.

9. The process according to claim 1 wherein the bacterial strain is selected from the group consisting of *Bordetella pertussis*, *Neisseria meningitidis*, *Cornyebacterium diphtheriae*, *Clostridium tetani*, *Clostridium difficile*, *Helicobacter pylori*, *Haemophilus influenzae*, *Staphylococcus aureus*, *Streptococcus pneumoniae*, *Salmonella* species, *Spirochetes* species, *Legionella* species and *Mycobacterium tuberculosis*.

10. The process according to claim 9 wherein the bacterial strain is selected from the group consisting of *Neisseria meningitidis* serogroup A, *Neisseria meningitidis* serogroup B, *Neisseria meningitidis* serogroup C, *Neisseria meningitidis* serogroup W135 and *Neisseria meningitidis* serogroup Y.

11. The process according to claim 10 wherein the bacterial strain is *Neisseria meningitidis* serogroup B.

12. The process according to claim 9 wherein the bacterial strain is a strain of *Streptococcus pneumoniae*.

13. The process according to claim 12 wherein the bacterial strain is *Streptococcus pneumoniae* serotype 1, 4, 5, 6A, 6B, 7F, 9V, 12F, 14, 15C, 33F, 18C, 19A, 19F, 22F or 23.

14. A process for producing a biopolymer or an aggregate of biopolymers including the steps of i) culturing a bacterial strain according to claim 1, and ii) harvesting the biopolymer or aggregate thereof from the culture medium or filtrate.

15. The process for producing a biopolymer or aggregate thereof according to claim 14, which comprises a further step of conjugating the biopolymer or aggregate thereof to a saccharide.

16. The process for producing a biopolymer or aggregate thereof according to claim 14, which comprises a further step of conjugating the biopolymer or aggregate thereof to a carrier protein.

17. A process for producing a vaccine comprising the steps of 1) producing a biopolymer or aggregate thereof using the process of claims 14, and 2) formulating the biopolymer or aggregate thereof as a vaccine by adding a pharmaceutically-acceptable excipient.

* * * * *